(12) United States Patent
Partington et al.

(10) Patent No.: US 12,594,395 B2
(45) Date of Patent: Apr. 7, 2026

(54) PATIENT INTERFACES WITH CONDENSATION REDUCING OR COMPENSATING ARRANGEMENTS

(71) Applicant: Fisher & Paykel Healthcare Limited, Auckland (NZ)

(72) Inventors: Andrew John Partington, Auckland (NZ); Peter Kenneth Graham, Auckland (NZ); Mark John Arrowsmith, Auckland (NZ); Christopher Earl Nightingale, Auckland (NZ); Vitaly Kapelevich, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 787 days.

(21) Appl. No.: 17/932,175

(22) Filed: Sep. 14, 2022

(65) Prior Publication Data

US 2023/0010318 A1     Jan. 12, 2023

Related U.S. Application Data

(63) Continuation of application No. 16/502,784, filed on Jul. 3, 2019, now Pat. No. 11,471,637, which is a (Continued)

(51) Int. Cl.
*A61M 16/06* (2006.01)
*A61M 16/00* (2006.01)
(Continued)

(52) U.S. Cl.
CPC .... *A61M 16/0808* (2013.01); *A61M 16/0057* (2013.01); *A61M 16/06* (2013.01); (Continued)

(58) Field of Classification Search
CPC ......... A47D 13/08; A61D 7/04; A61F 2/0004; A61F 2/07; A61F 2/88; A61F 2/95; A61F 2/9522; A61F 2/9526; A61F 2/958; A61F 2/966; A61F 2002/075; A61F 2210/0019; A61F 2250/0008; A61F 5/05891; A61F 5/3707; A61G 13/12; A61G 13/121; (Continued)

(56) References Cited

U.S. PATENT DOCUMENTS 2,254,854 A * 9/1941 O'Connell ............ A61M 16/06
128/206.28
2,749,910 A * 6/1956 Faulconer, Jr. ........ A61H 31/02
601/44
(Continued)

FOREIGN PATENT DOCUMENTS

EP          1516643      3/2005
WO     2011077250 A1     6/2011

*Primary Examiner* — Annette Dixon
(74) *Attorney, Agent, or Firm* — VIA LLP

(57)          ABSTRACT

Mask assemblies, breathing circuits and related components for respiratory therapy systems include configurations for reducing condensation within the mask and/or inhibiting or preventing condensation from coming into contact with a user of the mask. The mask assemblies can incorporate heating elements (such as heating coils), insulating spaces or barrier layers.

12 Claims, 32 Drawing Sheets

Related U.S. Application Data continuation of application No. 14/772,765, filed as application No. PCT/NZ2014/000024 on Mar. 4, 2014, now Pat. No. 10,357,627.

(60) Provisional application No. 61/772,432, filed on Mar. 4, 2013.

(51) Int. Cl.
A61M 16/08 (2006.01)
A61M 16/10 (2006.01)

(52) U.S. Cl.
CPC .... *A61M 16/0605* (2014.02); *A61M 16/0611* (2014.02); *A61M 16/0622* (2014.02); *A61M 16/0816* (2013.01); *A61M 16/0875* (2013.01); *A61M 16/1045* (2013.01); *A61M 16/1095* (2014.02); *A61M 2205/14* (2013.01); *A61M 2205/3653* (2013.01)

(58) Field of Classification Search
CPC ............ A61H 11/00; A61H 2201/0134; A61H 2201/0161; A61H 2201/0207; A61H 2201/0214; A61H 2201/0228; A61H 2201/0257; A61H 2201/0278; A61H 2201/0285; A61H 2201/0292; A61H 2201/1604; A61H 2201/1645; A61H 2201/165; A61H 2201/5071; A61H 2201/5082; A61H 2205/022; A61H 2205/025; A61H 23/00; A61H 23/0263; A61H 31/02; A61H 9/0078; A61M 16/0048; A61M 16/0057; A61M 16/0066; A61M 16/01; A61M 16/04; A61M 16/0436; A61M 16/0438; A61M 16/0475; A61M 16/06; A61M 16/0605; A61M 16/0611; A61M 16/0616; A61M 16/0622; A61M 16/0627; A61M 16/0633; A61M 16/0638; A61M 16/0655; A61M 16/0666; A61M 16/0683; A61M 16/0694; A61M 16/0808; A61M 16/0816; A61M 16/0833; A61M 16/0841; A61M 16/085; A61M 16/0875; A61M 16/104; A61M 16/1045; A61M 16/1065; A61M 16/107; A61M 16/1075; A61M 16/1085; A61M 16/1095; A61M 16/208; A61M 2016/0027; A61M 2016/003; A61M 2016/0661; A61M 2205/02; A61M 2205/0216; A61M 2205/0227; A61M 2205/0238; A61M 2205/0266; A61M 2205/07; A61M 2205/14; A61M 2205/15; A61M 2205/3331; A61M 2205/3368; A61M 2205/36; A61M 2205/3653; A61M 2205/3673; A61M 2205/59; A61M 2207/00; A61M 2207/10; A61M 2210/0606; A61M 2210/0618; A61M 2210/0625; A61M 2210/083; A61M 2230/432; A62B 18/02; A62B 18/025; A62B 18/04; A62B 18/08; A62B 18/082; A62B 18/084; B29C 33/3814; B29C 33/424; B29C 41/04; B29C 41/52; B29K 2995/0097; B29L 2025/00; B29L 2031/4835; B29L 2031/7102; B29L 2031/753; Y10S 152/02; Y10T 29/49927
See application file for complete search history.

(56) References Cited

U.S. PATENT DOCUMENTS

| | | | | |
|---|---|---|---|---|
| 3,595,228 A * | 7/1971 | Simon | A61M 16/021 | |
| | | | 340/687 | |
| 3,613,792 A * | 10/1971 | Hyde | E21B 33/10 | |
| | | | 166/57 | |
| 5,592,938 A * | 1/1997 | Scarberry | A61M 16/06 | |
| | | | 128/206.25 | |
| 5,660,174 A * | 8/1997 | Jacobelli | A61M 16/0616 | |
| | | | 128/206.24 | |
| 6,834,650 B1 * | 12/2004 | Fini | A61M 16/06 | |
| | | | 128/206.26 | |
| 6,860,268 B2 * | 3/2005 | Bohn | A61M 16/0633 | |
| | | | 128/206.26 | |
| 8,336,549 B2 * | 12/2012 | Nashed | A61M 16/0605 | |
| | | | 128/203.29 | |
| 8,757,150 B2 * | 6/2014 | Davidowski | A61M 16/0638 | |
| | | | 128/200.24 | |
| 11,471,637 B2 * | 10/2022 | Partington | A61M 16/0611 | |
| 2009/0014007 A1 | 1/2009 | Brambilla | | |
| 2010/0024811 A1 * | 2/2010 | Henry | A61M 16/0622 | |
| | | | 128/202.16 | |
| 2010/0154798 A1 * | 6/2010 | Henry | A61M 16/065 | |
| | | | 128/206.24 | |
| 2011/0247628 A1 | 10/2011 | Ho | | |
| 2021/0402121 A1 * | 12/2021 | McAuley | A61M 16/1075 | |

* cited by examiner

1

PATIENT INTERFACES WITH CONDENSATION REDUCING OR COMPENSATING ARRANGEMENTS

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

BACKGROUND OF THE INVENTION

Field of the Invention

The present disclosure relates generally to respiratory therapy systems. In particular, the present disclosure relates to patient interfaces, such as mask assemblies and breathing circuits, with condensation reducing or compensating configurations.

Description of the Related Art

CPAP therapy, commonly used to treat obstructive sleep apnea, pumps air to a patient to maintain a minimum pressure in the airways. Often the air is heated and humidified before being sent to the patient. This causes less dryness and irritation to the patient and can increase compliance in the therapy. An issue with humidified air is that it can condense into water, becoming rainout. This is due to the heated air cooling down and the air reaches a dew point, causing condensation.

Rainout can cause several problems, including the following: the water can restrict airflow to the patient or out of the mask; water can form into droplets and drip on a patients face which can wake them; a whistling noise can result when water forms on the vent holes; water can disrupt the mask seal against the patient's face; the patient may wake with a wet face which can feel unpleasant.

If a patient is unhappy with the rainout in their mask, they may reduce the humidification settings in their CPAP or turn off humidification entirely. Other advice to reduce rainout is to increase the temperature of the bedroom so that there is a smaller temperature drop between the humidified air and the ambient air of the room and thus less water will condense.

SUMMARY OF THE DISCLOSURE

To prevent rainout in breathing tubes there are several technologies used in CPAP tubing, such as the heated breathing tube and insulating covers that can go over the tubes. However there are currently no technologies and little in the state of the art to prevent condensation at the mask region. One or more of the disclosed masks, breathing circuits or related components address the issue of condensation at the mask.

Mask assemblies, breathing circuits and related components described herein include configurations for reducing condensation within the mask and/or inhibiting or preventing condensation from coming into contact with a user of the mask. The mask assemblies can incorporate heating elements (such as heating coils), insulating spaces or barrier layers.

The systems, methods and devices described herein have innovative aspects, no single one of which is indispensable or solely responsible for their desirable attributes. Without limiting the scope of the claims, some of the advantageous features will now be summarized.

In accordance with at least one of the embodiments disclosed herein, a patient interface is provided comprising a body adapted to form a seal with a user's face, a coupling for fluid connection to a gas delivery system, a water vapor breathable layer, and an outer layer with holes that allows gases to flow into an intermediary chamber between the water vapor breathable layer and the outer layer.

In some configurations, the patient interface further comprises a vent that allows a flow of gases from an interior of the body to an exterior of the body. The vent can be configured so that the flow of gases entrains air from the environment into the intermediary chamber. In some configurations, the vent comprises a hydrophobic material and an area adjacent the vent can comprise a hydrophilic material.

The holes on the outer layer can be disposed at or near the perimeter of the outer layer. In some configurations, the body comprises a silicone seal member.

In accordance with at least one of the embodiments disclosed herein, a patient interface is provided comprising a body adapted to form a seal with a user's face, the body comprising an inner layer, an outer layer, and an insulation space between the inner and outer layers. The patient interface can comprise a coupling for fluid connection to a gas delivery system.

In some configurations, the patient interface further comprises a heating element disposed in the insulation space.

The patient interface can further comprise a vent that allows a flow of gases from an interior of the body to an exterior of the body. The vent can be recessed and disposed adjacent the inner layer. The insulation space can be in fluid communication with the vent. The body can be configured so that the flow of gases flows through the insulation space before exiting the interface.

In some configurations, the outer layer is releasably attached to the inner layer. The patient interface can further comprise at least one heat pad coupled to the outer layer.

In some configurations, the patient interface further comprises a phase change material in the insulation space.

The inner layer can be configured to diffuse gases from the gas delivery system and can be heated by the gases.

In accordance with at least one of the embodiments disclosed herein, a patient interface is provided comprising a foamed breathable membrane body that allows water vapor to pass through the body, a frame structure attached to the foamed breathable membrane body, and a coupling for fluid connection to a gas delivery system.

In some configurations, the patient interface further comprises a water vapor breathable layer. The patient interface can further comprise a vent that allows a flow of gases from an interior of the interface to an exterior of the interface. The patient interface can further comprise a seal adapted to form at least a substantial seal with a user's face.

In some configurations, the foamed breathable membrane body may be ribbed.

In accordance with at least one of the embodiments disclosed herein, a patient interface is provided comprising a body adapted to form a seal with a user's face, the body comprising an inner layer made of a thermally conductive material and an outer layer made of an insulating material. The patient interface can further comprise a coupling for fluid connection to a gas delivery system.

In some configurations, the patient interface further comprises a vent that allows a flow of gases from an interior of the body to an exterior of the body.

In some configurations, the patient interface further comprises a heating element in thermal communication with the inner layer. The thermally conductive material can be a polymer. The thermally conductive material can be a metal.

In some configurations, the patient interface further comprises a thermoelectric cooling device in thermal communication with the inner layer. The patient interface can further comprise a sensor to provide feedback of the temperature of the inner layer.

BRIEF DESCRIPTION OF THE DRAWINGS

The drawings are provided to illustrate example embodiments described herein and are not intended to limit the scope of the disclosure.

DETAILED DESCRIPTION OF SPECIFIC EMBODIMENTS

Figure 1:
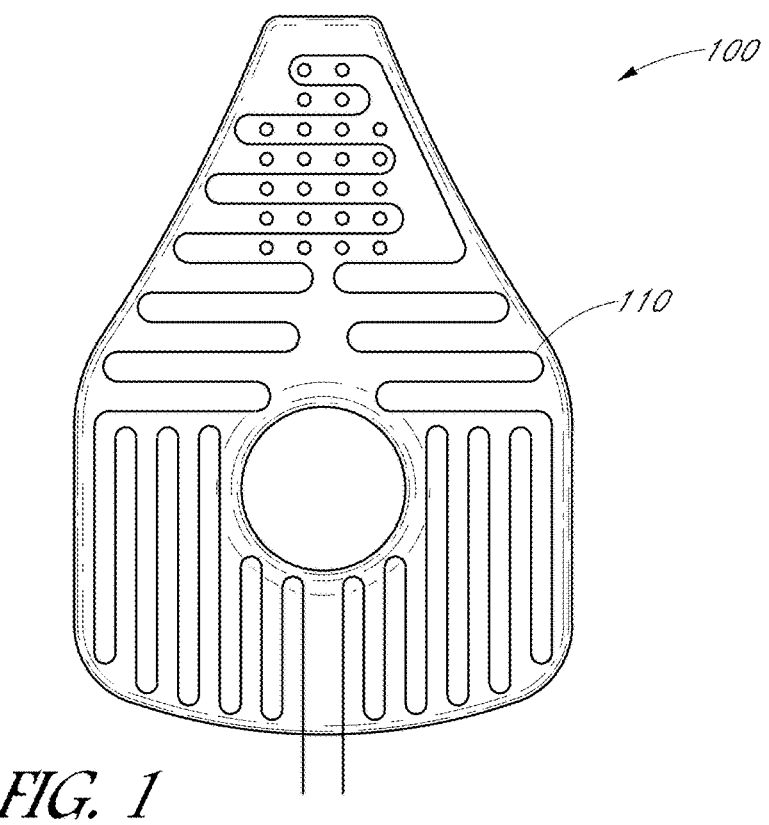
FIGS. 1-2 are front views of mask assemblies with heating elements winding through the mask, according to embodiments of the present disclosure.
Figure 2:
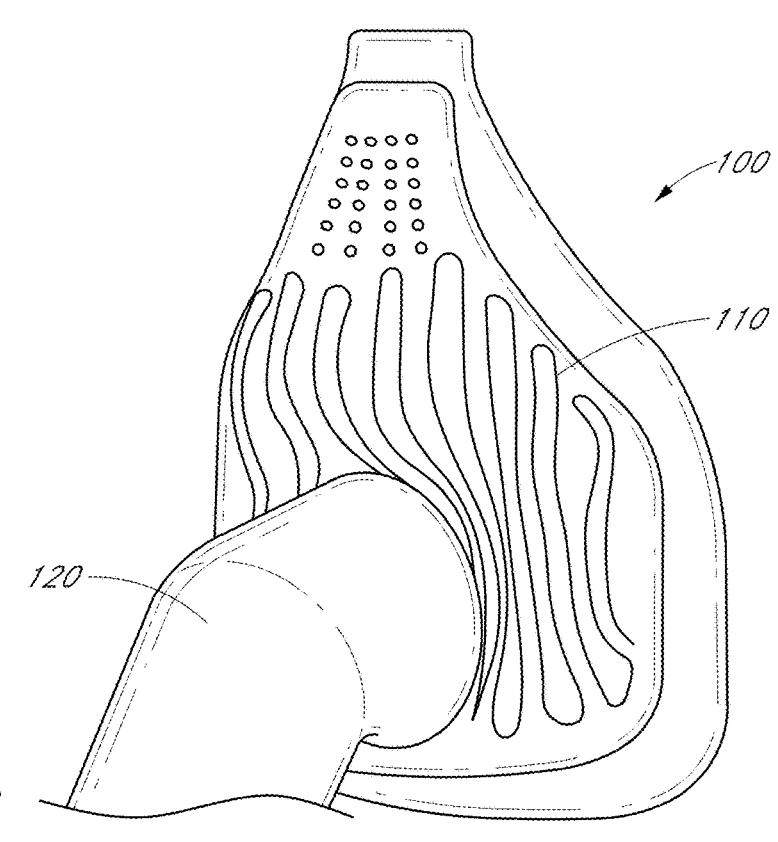

FIGS. 1 and 2 illustrate interfaces, specifically mask assemblies 100, comprising heating elements 110, such as for example heating coils. The heating elements 110 can be moulded into the mask as in the illustrated configuration, or otherwise secured to the mask such as through adhesives, clips, welding or the like. In some configurations, the heating elements are attached to the inner surface of the mask. The heating elements 110 can wind throughout a substantial portion or all of the mask's inner surface. Preferably the heating elements are sufficiently distributed on the surface area of the mask to evenly or substantially evenly heat the interior space of the mask.

The heating elements 110 can be powered by the electrical current from the CPAP or other flow generator/humidifier system. Power can be supplied directly to the mask assembly 100 such as via a separate power line. In some configurations, the power can be conveyed through another component of the system, such as the breathing tube 120 or circuit, for example.

Figures 46, 47, 48:
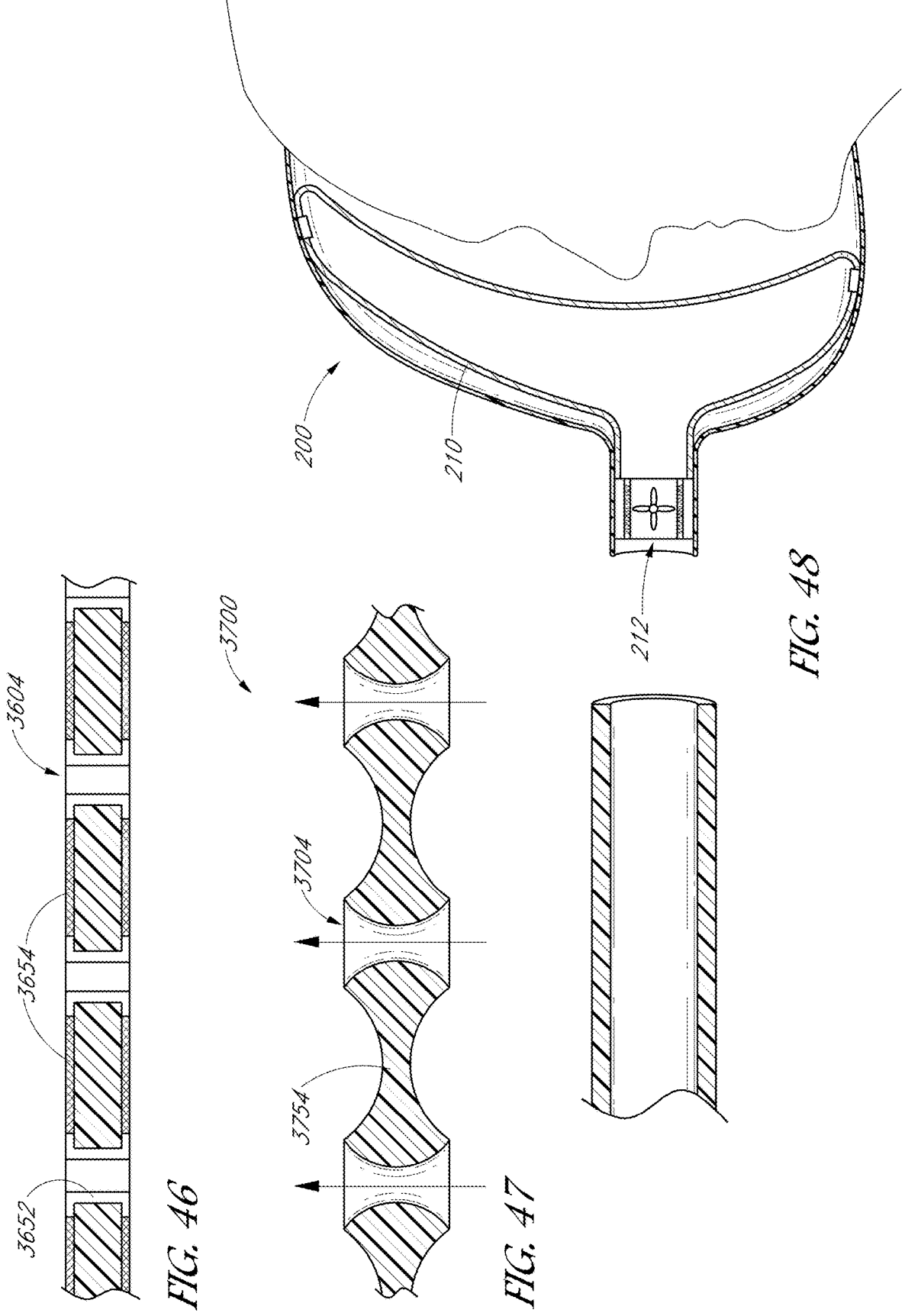
FIG. 46 is a close-up cross-sectional side view of the inserts of FIG. 45.
FIG. 47 is a close-up cross-sectional side view of vent holes with peaks and depressions, according to an embodiment of the present disclosure.
FIG. 48 is a cross-sectional side view of a mask assembly with a generator, according to an embodiment of the present disclosure.
Figure 49:
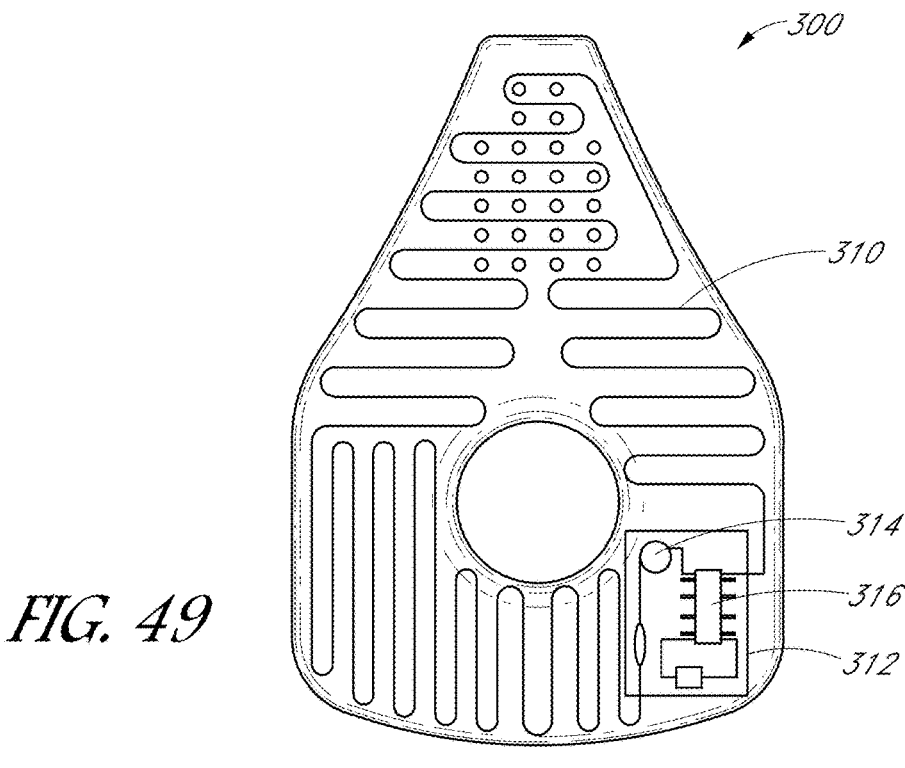
FIG. 49 is a front view of a mask assembly with a circuit board, according to an embodiment of the present disclosure.

FIGS. 48 and 49 illustrate mask assemblies comprising heating elements with alternative or auxiliary power configurations for powering the heating elements. With reference to FIG. 48, heating elements 210 (e.g., copper wire or other conductive material) is heated with current produced in a small generator 212 in the mask assembly 200. The generator 212 can comprise any suitable configuration, such as a small fan and motor placed in the mask so that airflow from the CPAP (or other flow generator) will cause the fan blades to rotate (or otherwise power the generator). The rotation will produce an electrical current that passes through the heating element 210.

FIG. 49 illustrates a mask assembly 300 with in-moulded heating elements 310 (e.g., copper coils or other conductive material) that form a circuit with a circuit board 312 attached to a suitable location (e.g., the exterior) of the mask. The circuit board 312 can contain a battery 314 to power the heating element 310 with current and, optionally, a microcontroller and/or sensors (such as a temperature sensor) to allow smart control of the heating element 310.

Figure 3:
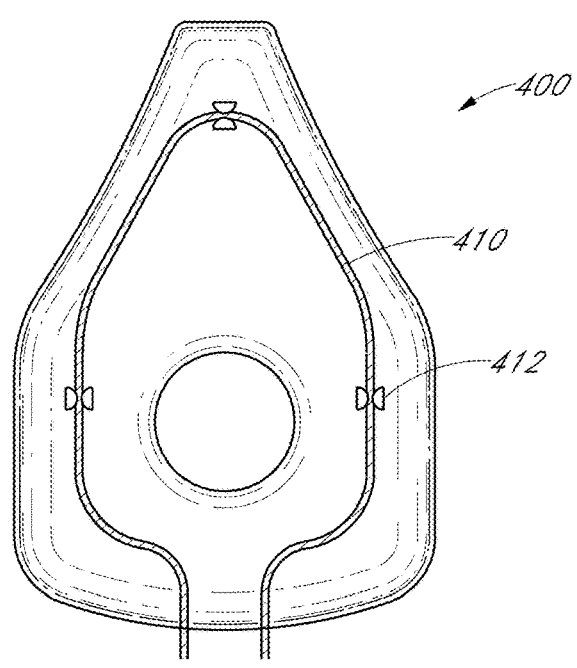
FIG. 3 is a front view of a mask assembly with a loop of heating element, according to an embodiment of the present disclosure.
Figure 4:
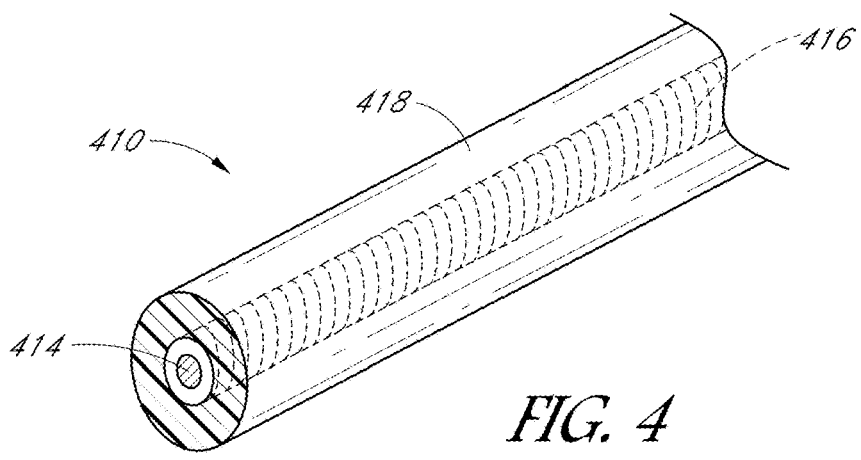
FIG. 4 is a close-up perspective view of a section of a heating element, according to an embodiment of the present disclosure.
Figure 5:
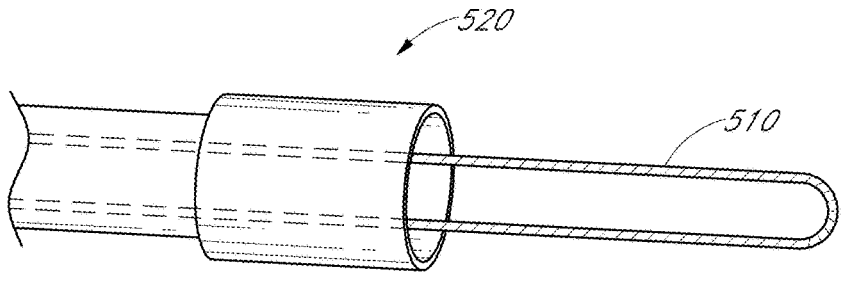
FIG. 5 is a side view of a breathing circuit with a heating element, according to an embodiment of the present disclosure.

FIG. 3 illustrates a mask assembly 400 having one or more loops of heating element 410. The one or more loops of heating element 410 can be clamped in place by a retaining mechanism 412, such as plastic hooks or tabs, similar to the ones used to connect the mask strap to the mask in the GLIDER™ strap configurations used in the FLEXIFIT™ series nasal masks sold by Fisher & Paykel Healthcare. For example, a suitable configuration is disclosed in international patent publication number WO2011/077254 A2, especially in FIG. 27, the entirety of the publication which is incorporated by reference herein. The heating element can be of any suitable construction, such as the same as or similar to that used in the Evaqua 2™ breathing circuit sold by Fisher & Paykel Healthcare. FIG. 4 illustrates a section of an example of a suitable heating element 410, which comprises a core 414 with conductive coil 416 (e.g., copper) wound around it, and an outer cover 418 around the core. In some configurations, the core can be made of string and the outer cover can be a plastic tube.

Although the illustrated interfaces are full face masks, the scope of the present disclosure should not be limited by the particular embodiments described. The interfaces can comprise any of a plurality of different types of suitable mask configurations. For example, certain features, aspects and advantages of the present invention can be utilized with nasal masks, full face masks, oronasal masks or any other positive pressure mask.

FIGS. 5-11 illustrate breathing circuits, masks and related components for heated mask assemblies. With respect to FIG. 5, a breathing tube 520 can have at least one length of heating element 510 (e.g., coiled heating wire) disposed inside the tube, which can extend at least partially outside the tube. The portion of the heating element that extends outside the tube can be clipped into a mask and used as a heating element for the mask, as described previously for FIG. 3. In the illustrated configuration, a loop of heating element 510 is configured to be positioned in the interior of the mask with the end portions of the heating element being positioned outside of the mask. In other configurations, a single length of heating element can have conducting wires creating a circuit, or multiple lengths or loops of heating elements can be provided to be positioned into the mask.

Figure 6:
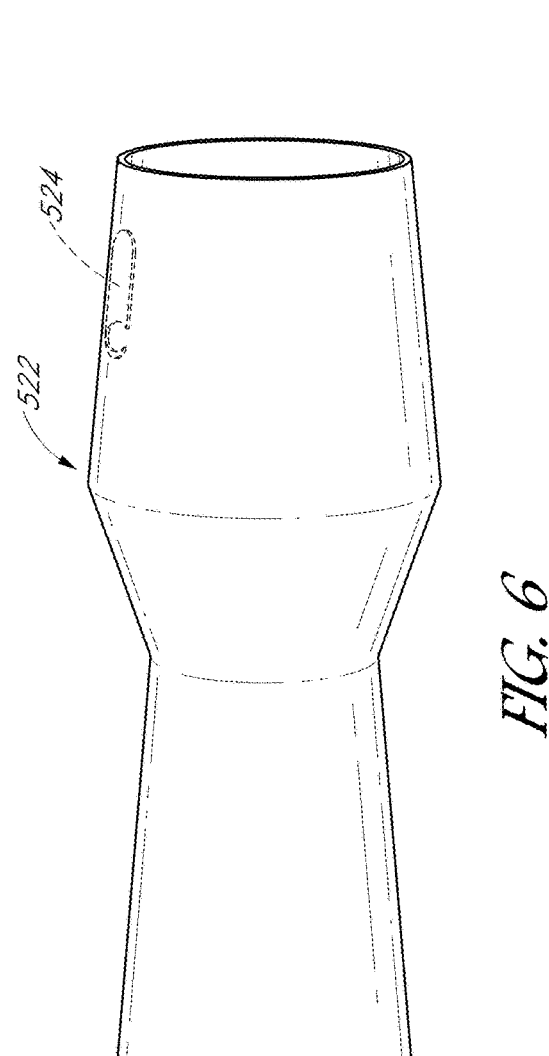
FIG. 6 is a side view of a cover for a breathing tube, according to an embodiment of the present disclosure.
Figure 7:
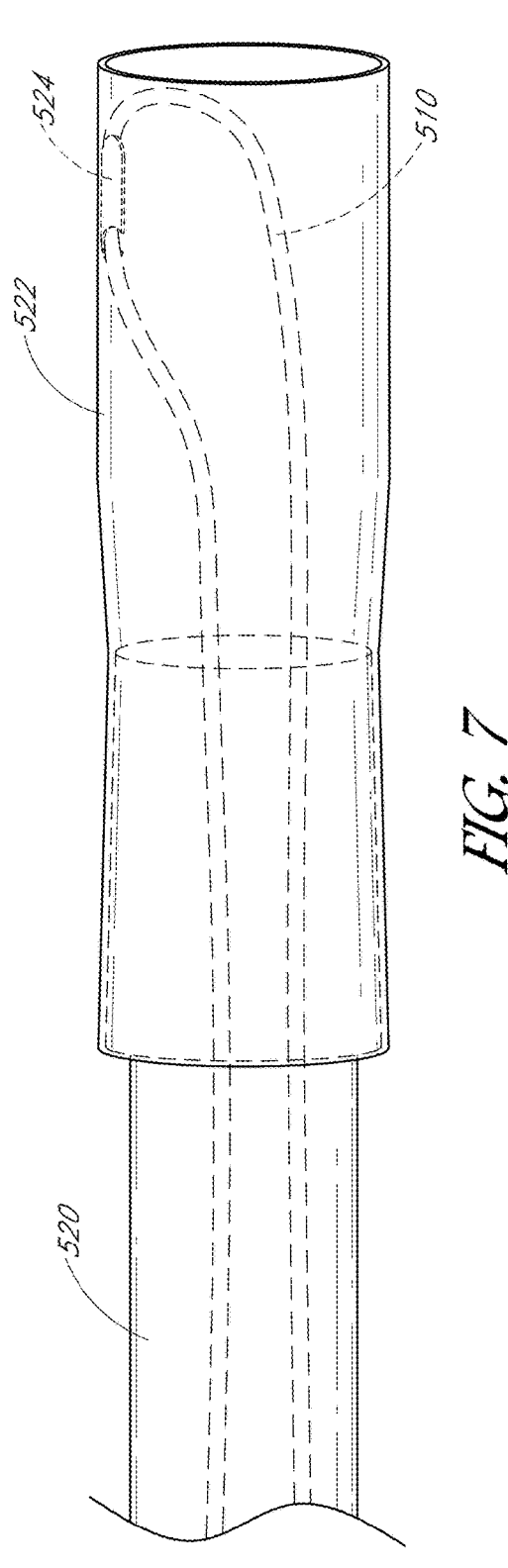
FIG. 7 is a side view of the cover of FIG. 6 attached to the breathing circuit of FIG. 5.

With respect to FIGS. 6 and 7, a cover 522 can be placed at the end of the breathing tube 520 so that the portion of heating element 510 extending outside the breathing tube 520 is contained when a non-heated mask is to be connected to the breathing tube 520. The cover 522 can have two tapered connections. At one end the cover 522 can be tapered to connect onto the breathing tube 520 and the other end can be tapered to connect onto the mask. A clip 524 can be disposed on the interior of the cover 522 so that the heating element 510 can be clipped and held in place within the cover 522. The clip can be made of plastic, metal, or other suitable material and can be moulded, welded, adhered, or otherwise attached to the cover. An embodiment of a cover 522 is shown by itself in FIG. 6 and coupled to a breathing tube 520 in FIG. 7.

Figure 8:
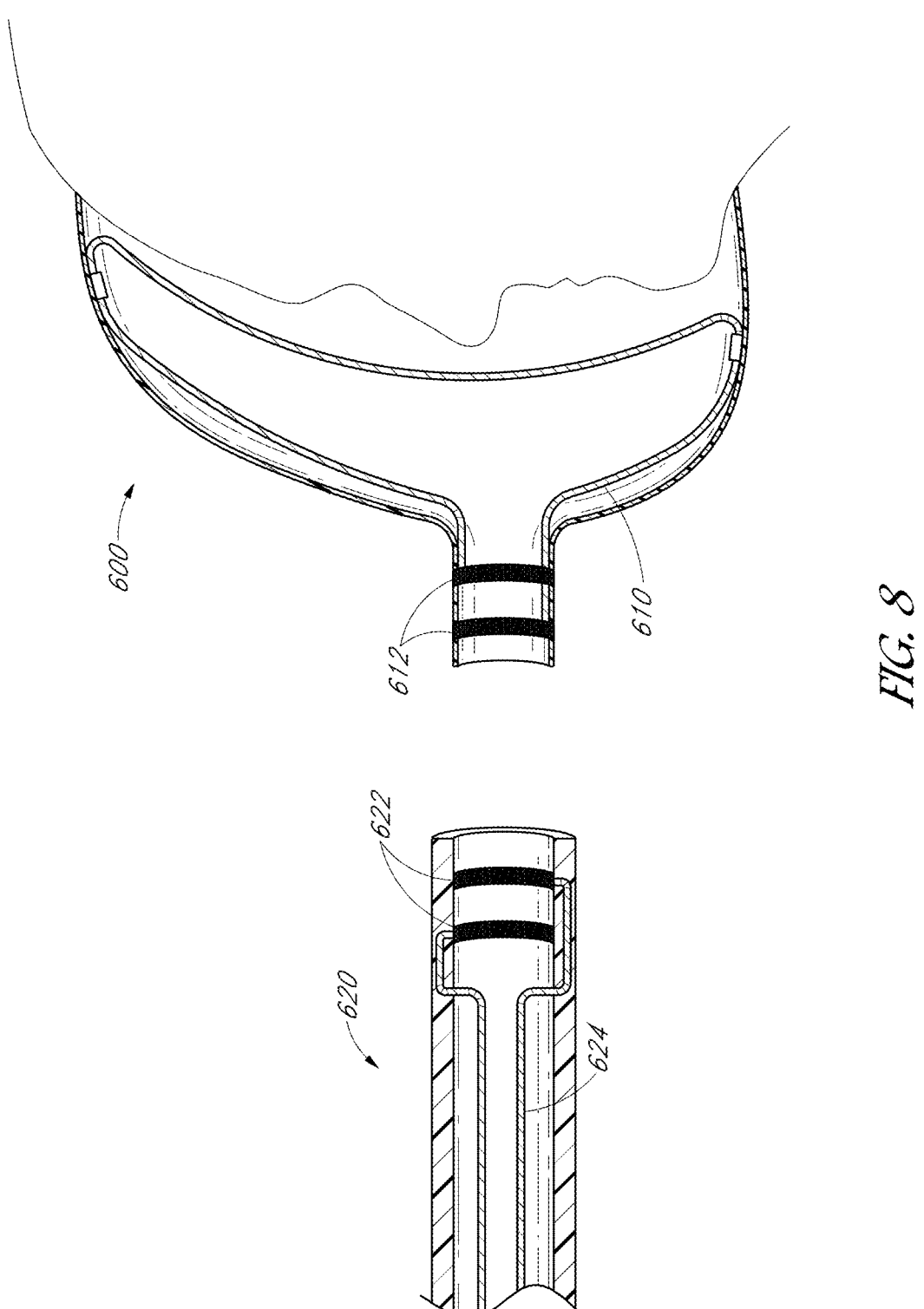
FIGS. 8-10 are cross-sectional side views of connections between mask assemblies and breathing tubes, according to various embodiments of the present disclosure.

With respect to FIG. 8, the breathing tube 620 can have two or more rings 622 exposed on its interior that are made of for example copper, silver or other conductive material. The breathing tube rings 622 can be in electrical communication with conductive wires 624 that extend inside the tube. In some configurations, the wires 624 can be partially disposed within the tube's wall and connected to the outer surface of the breathing tube rings 622. In some configurations, the conductive wires can be at least partially made of a heating element material to help regulate condensation in the tube. The breathing tube 620 can be configured to couple with a mask assembly 600 having two or more mask rings 612 that lie exposed on the outside surface of the mask assembly 600. The breathing tube rings 622 can come into contact with the mask rings 612 when the breathing tube 620 is coupled to the mask assembly 600 to form an electrical connection. The mask rings 612 can be connected to wires 610, which may be at least partially made of heating elements, which extend to the interior of the mask assembly 600. The wires 610 can be connected to the interior surface of the mask rings 612, allowing the breathing tube 620 to rotate in relation to the mask assembly 600 while still maintaining an electrical connection.

Figure 9:
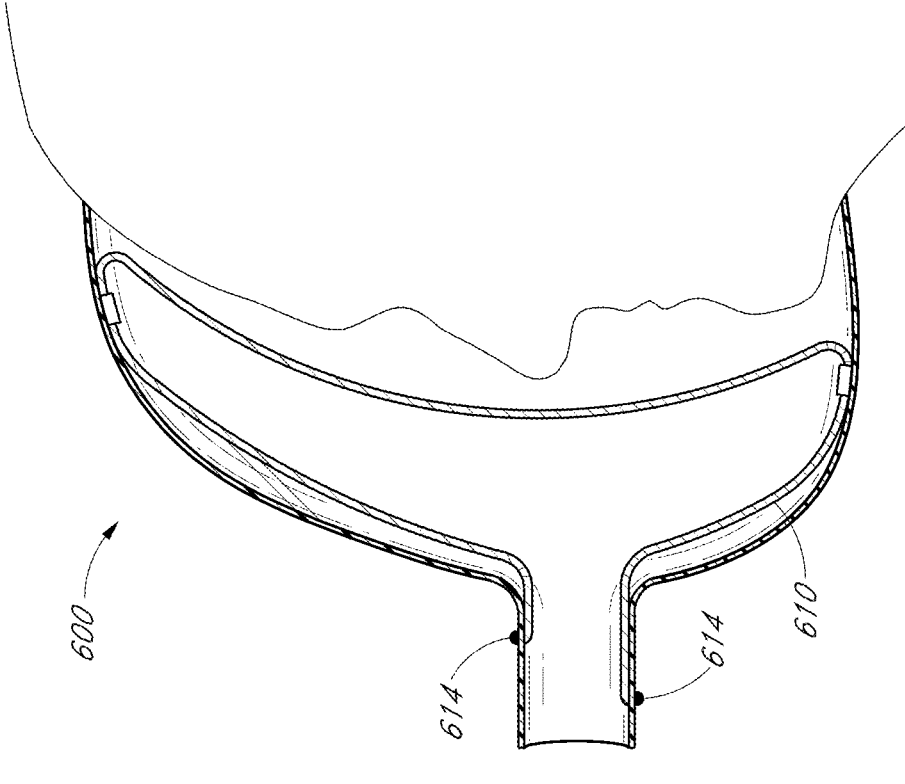
Figure 9:
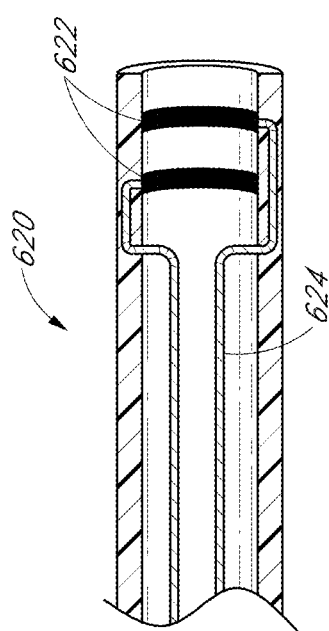

FIG. 9 illustrates a similar configuration as the embodiment in FIG. 8, except with a brush connection 614 on the mask assembly 600 side of the connection. In some configurations, the brush connection can be on the tube side of the connection and the mask assembly side can have a ring. The brush connection 614 can comprise a conductive brush (e.g., copper brush) that is exposed, or a protrusion with conductive material (e.g., copper) that can come into contact with the connecting ring to make an electrical contact between the two connections.

Figures 10, 10A:
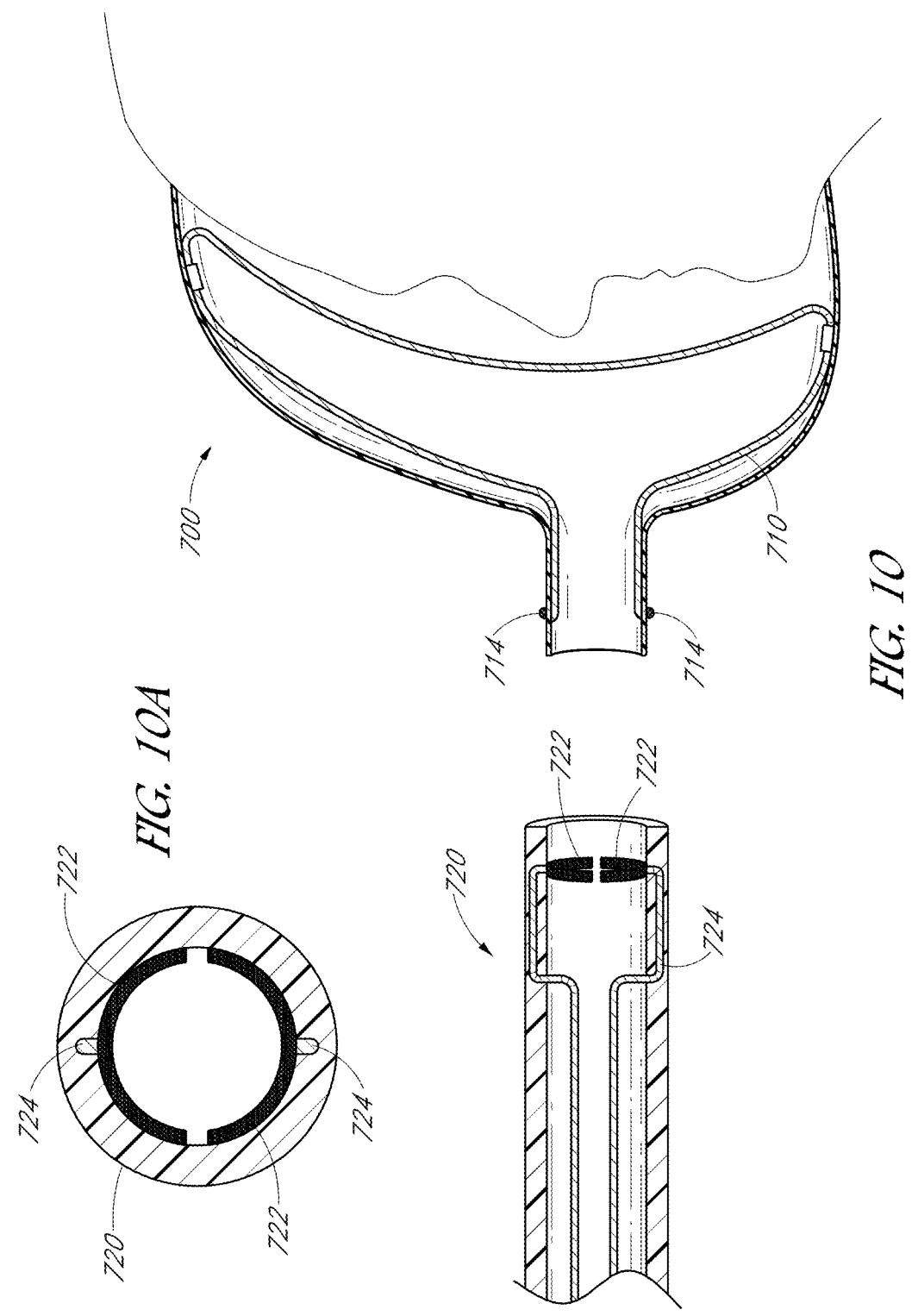
FIG. 10A is a front sectional view of the breathing tube of FIG. 10.

With respect to the breathing tube 720 and mask assembly 700 of FIG. 10, two or more half rings 722 and two or more brushes 714 can be employed. This is a simpler connection and advantageously requires less conductive material compared to full rings. FIG. 10A illustrates a view of the end of the breathing tube 720 showing the half rings 722 and the conductive wires 724 extending from the half rings. Such a configuration may not be preferred in certain applications because if the brushes 714 are positioned exactly at the point where a gap exists between the half rings 722, the electrical connection could be lost until the connection is made again.

However, in some applications, this position may be unlikely to occur or, if it occurs, is unlikely to occur for a significant period of time.

Figure 11:
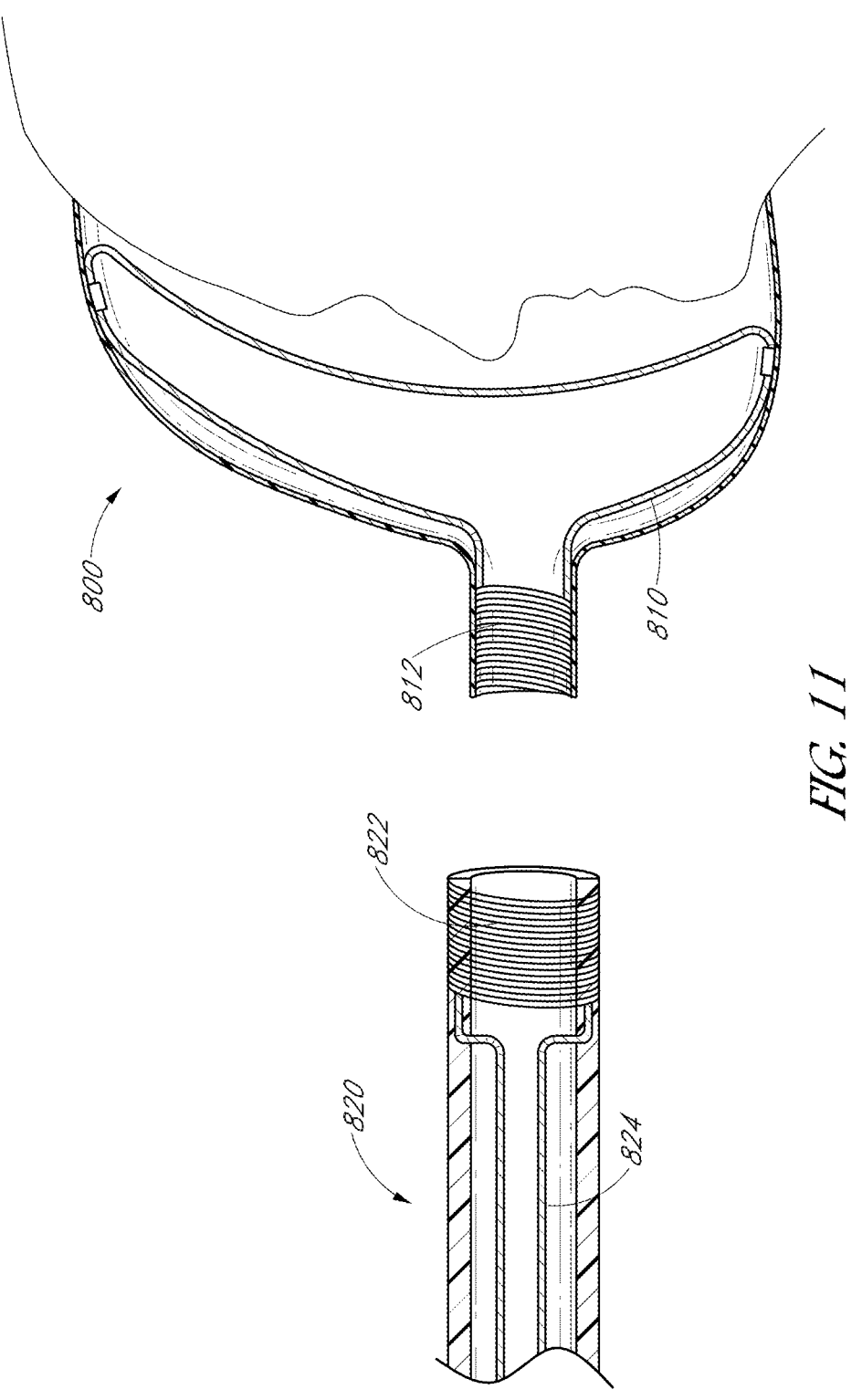
FIG. 11 is a cross-sectional side view of a connection between a mask assembly and a breathing tube, according to another embodiment of the present disclosure.

With respect to FIG. 11, electromagnetic induction can also be used to transmit energy to the mask assembly 800 and induce a current. By winding conductive wires tightly around the connection at the breathing tube 820, the current in the tube windings 822 can induct a magnetic field. The mask assembly 800 can have mask windings 812 that induce electrical current when the mask windings are positioned in the magnetic field produced by the tube windings 822, such as when the breathing tube 820 is connected to the mask assembly 800. In such configurations, the power source preferably is either a time-varying current or an alternating current (AC) in the tube and not DC.

In some configurations, the mask assembly can comprise reusable portions and disposable portions. For example, a reusable portion can comprise of one or more heating elements or coils of heater wire that can be over-moulded onto the reusable portion. Electrical connections can be configured to be connected to a heated breathing tube's wiring. The reusable portion of the mask assembly can couple onto the rest of the mask assembly, such as the mask seal or elbow, which may be disposable portions. Since the portion of the mask assembly containing heating elements is usually a more expensive component, it can be reused whereas other portions of the mask assembly can be disposable after a single use or for short term use (days, weeks, or months). This would be desirable in hospital usage, such as for patients requiring breathing support, as masks are designed to be single use only. With this configuration, portions of the mask assembly can still be kept disposable for sanitary reasons, but the high cost parts can be cleaned and reused. This allows a high cost part to be integrated with the mask system while reducing overall costs.

FIGS. 12-20 illustrate various configurations of a multi-layer mask, which is embodied as a double-layer mask assembly in the illustrated configurations. However, in other configurations, the mask can include more than two layers (e.g., three, four or more layers). In some configurations, air from the interior of the mask passes through a second chamber (insulation or transition space) defined between a first layer and a second layer (or other layers in a mask having more than two layers) before exiting the mask. The insulation or transition space provides insulation to the interior of the mask.

Figure 12:
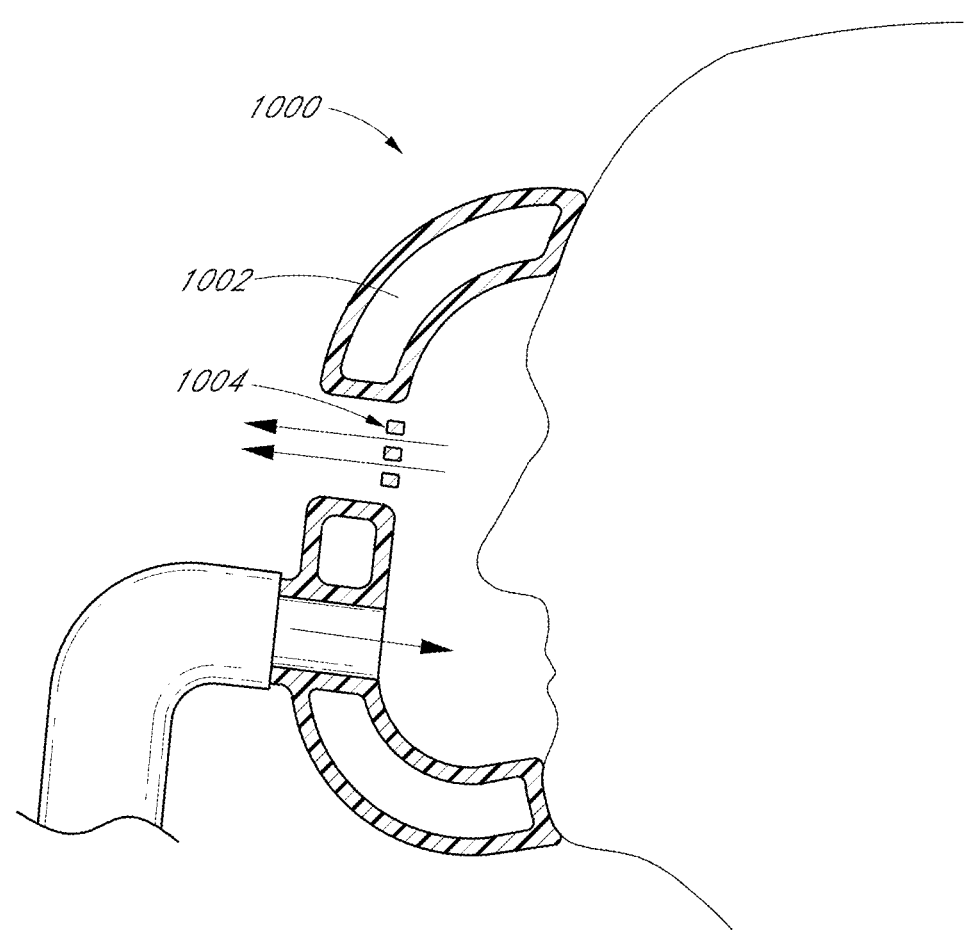
FIG. 12 is a cross-sectional side view of a double layer mask assembly, according to an embodiment of the present disclosure.
Figure 13:
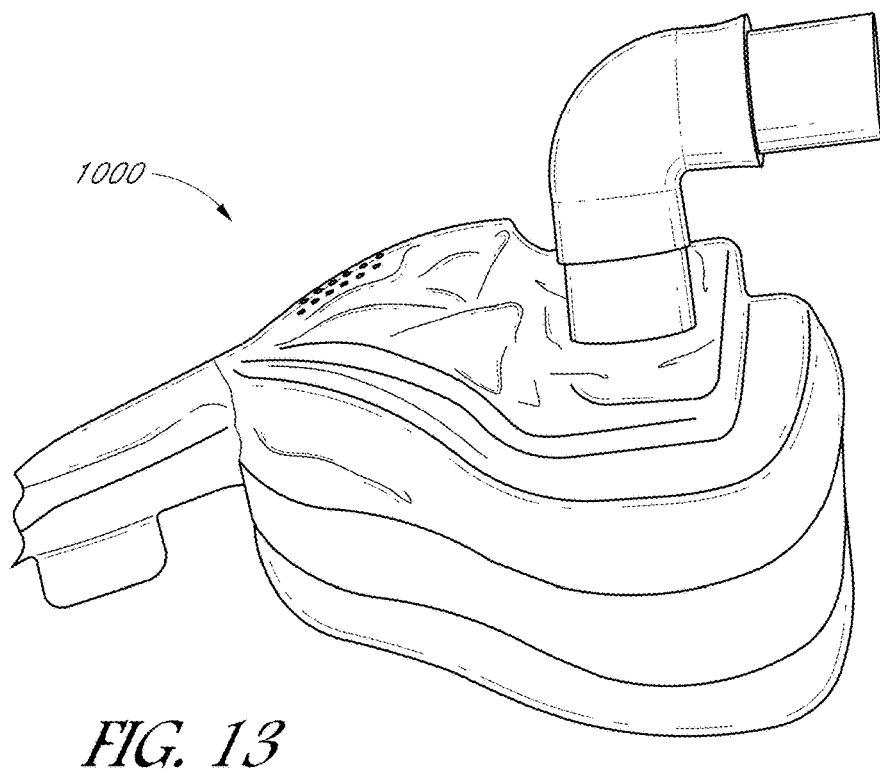
FIG. 13 is a side perspective view of a double layer mask assembly, according to an embodiment of the present disclosure.

With respect to FIGS. 12 and 13, the mask assembly 1000 can have two or more layers made of for example plastic, wherein an insulation space 1002 or transition space is defined by the space between the layers, which can be substantially or completely sealed from the interior and exterior of the mask. The insulation space 1002 can be filled with air or any other suitable gas or other medium that preferably provides an insulating function, such as a low conductivity fluid. As used herein, the term fluid is used to refer to liquids, gases or a combination of liquids and gases. In some configurations, the insulation space 1002 can be at least a partial vacuum having a pressure below atmospheric pressure. Fluids can leave the interior of the mask assembly 1000 via recessed vent holes 1004. By having the vent holes 1004 recessed, they have some insulation from the cold ambient air (cold at least relative to the supplied breathing gas) surrounding the mask assembly 1000 and therefore water condensation can be reduced.

Figure 14:
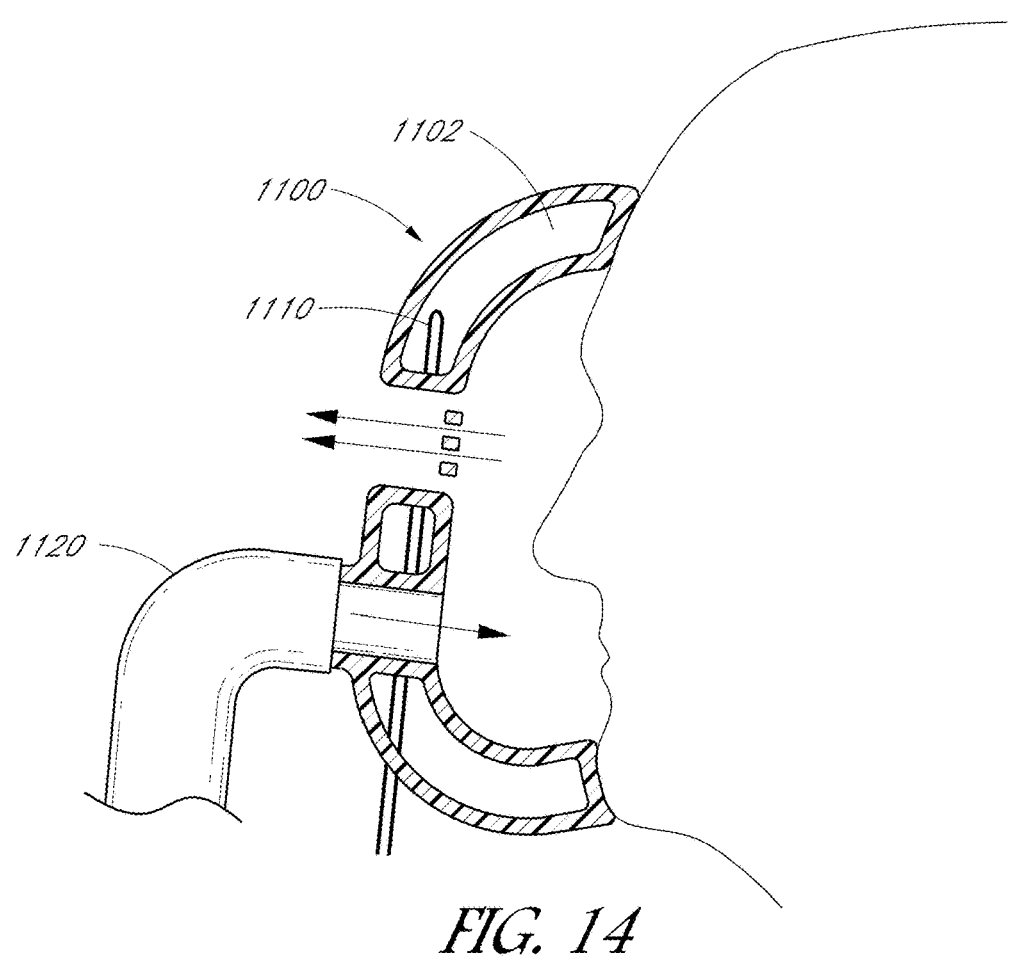
FIGS. 14-24 are cross-sectional side views of double layer mask assemblies, according to various embodiments of the present disclosure.

FIG. 14 illustrates a mask assembly 1100 that is similar to or the same as the previous mask of FIGS. 12 and 13, with a heating element 1110 (e.g., heated copper wire) extending into the insulation space 1102 between the layers of the mask assembly 1100. In some configurations, the heating element can extend from the breathing tube 1120. The heating element 1110 can heat the air inside the insulation space 1102, providing a heat barrier to the fluids inside the mask from the relatively colder outside air, thus reducing condensation within the inner layer of the mask.

Figures 15, 16:
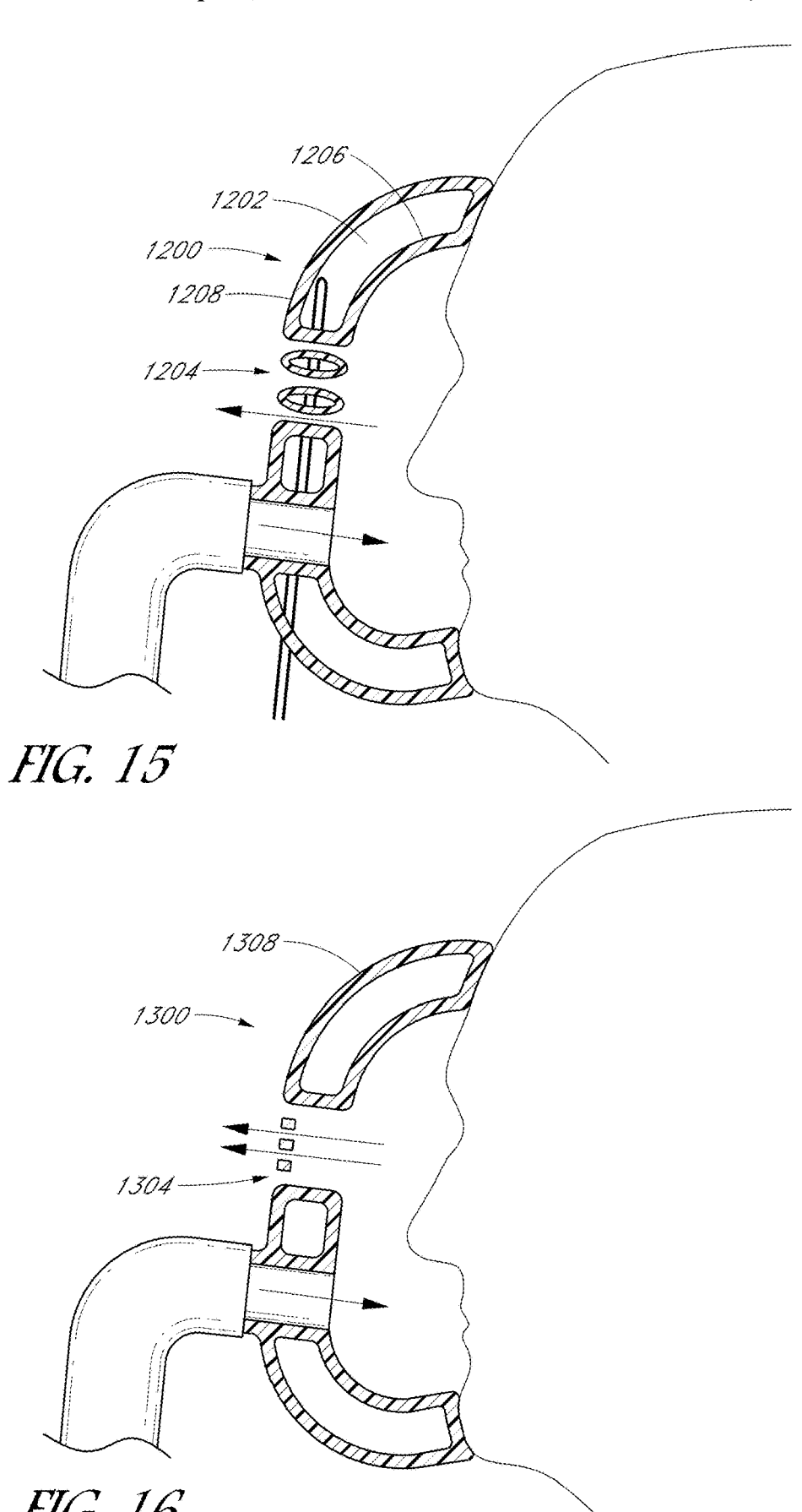

FIG. 15 illustrates a mask assembly 1200 that is similar to or the same as the previous masks of FIGS. 12-14 except the vent holes 1204 extend from the interior layer 1206 to the exterior layer 1208. The warmer air in the insulation space 1202 can go around the vent holes 1204 and keep them warm and reduce condensation.

FIG. 16 illustrates a mask assembly 1300 that is similar to or the same as the double layer mask assembly of FIG. 12 except the vent holes 1304 are on the exterior layer 1308 of the mask assembly 1300.

Figures 17, 18:
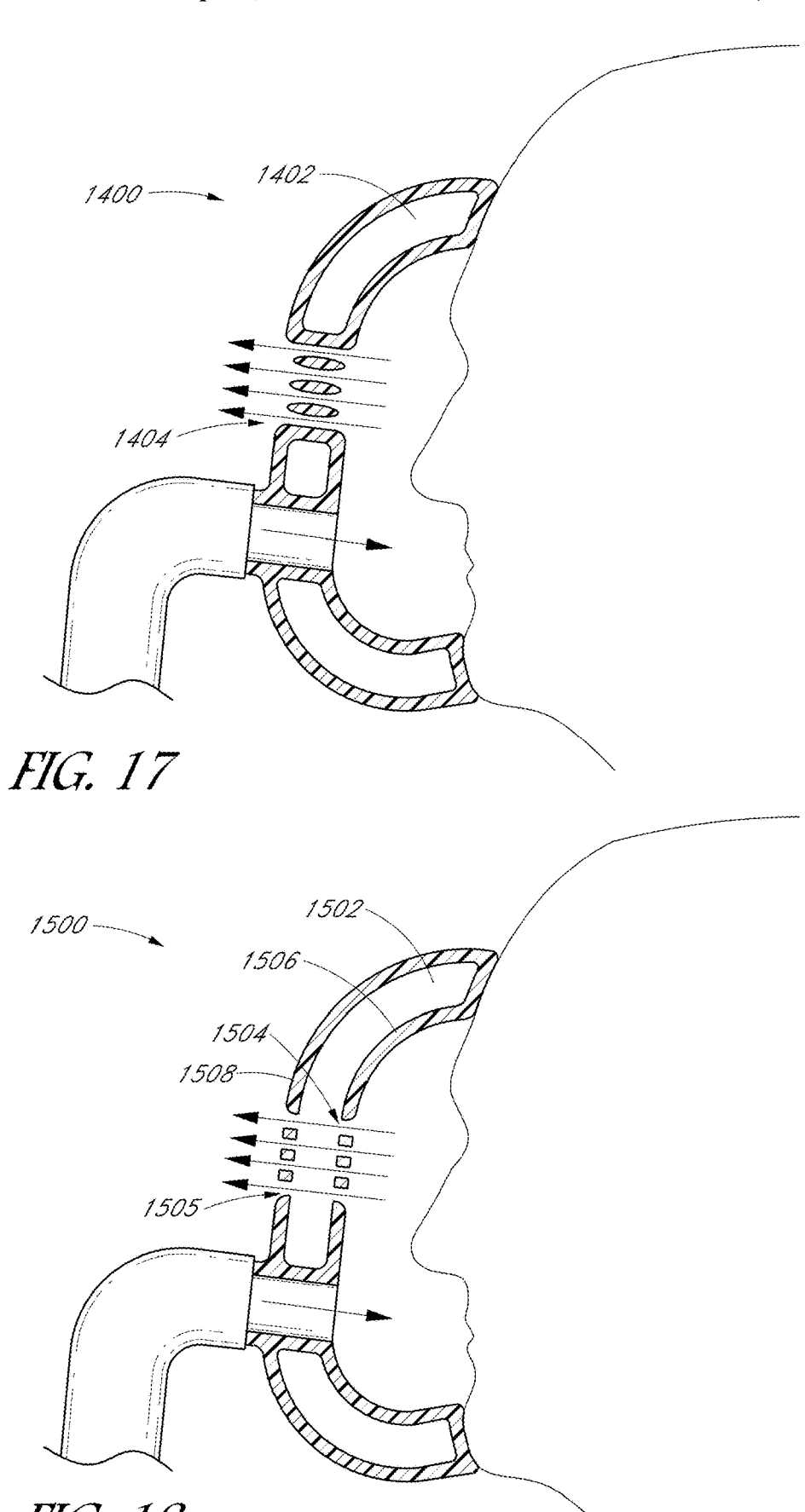

FIG. 17 illustrates a mask assembly 1400 that is similar to or the same as the mask assembly of FIG. 16 except the vent holes 1404 are long and extend the length of the two layers of the mask assembly. As explained before for FIG. 15, the warmer air in the insulation space 1402 can go around the vent holes 1404 and keep them warm and reduce condensation.

In the mask assembly 1500 of FIG. 18, fluids can enter the interior of the mask and travel through the insulation space 1502 before exiting out the mask. The fluids can travel through vent holes 1504 in the interior layer 1506 into the insulation space 1502 and through exhaust holes 1505 in the exterior layer 1508 of the mask assembly 1500. In some configurations, the vent holes 1504 of the interior layer 1506 and the exhaust holes 1505 of the exterior layer 1508 are aligned with one another. By traveling through the insulation space 1502, the fluids are kept warmer which can help reduce condensation.

Figures 19, 20:
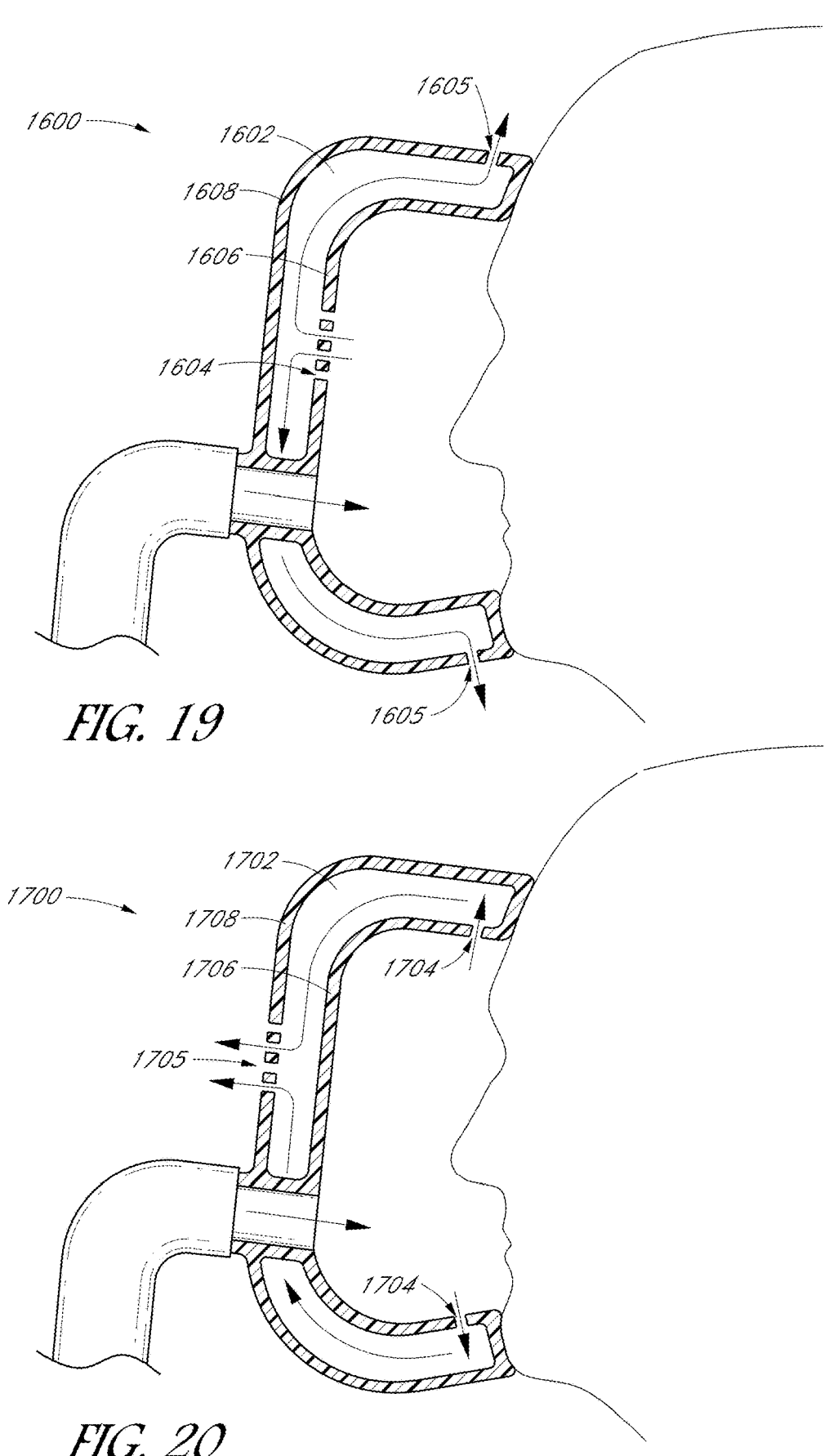

In the mask assembly 1600 of FIG. 19, fluids enter the interior of the mask and exit out through vent holes 1604 in the interior layer 1606 into the insulation space 1602. The fluids can travel through the insulation space 1602 and exit the mask assembly 1600 through exhaust holes 1605 in the exterior layer 1608. In some configurations, the exhaust holes 1605 can be at the sides of the mask assembly 1600 and positioned all around the circumference of the mask assembly. The vent holes 1604 of the interior layer 1606 may not be aligned with the exhaust holes 1605 of the exterior layer 1608.

The mask assembly 1700 illustrated in FIG. 20 is essentially the reverse of the previous mask assembly of FIG. 19. Fluids can enter the insulation space 1702 from the interior of the mask via vent holes 1704 disposed around the circumference of the interior layer 1706 of the mask and can exit the insulation space 1702 via exhaust holes 1705 on the exterior layer 1708 of the mask.

FIGS. 21-24 illustrate double mask assemblies in which the second layer is partially or completely detachable from the main part (e.g., first layer) of the mask. In the configuration illustrated in FIGS. 21 and 22, the second layer 1808 has a small protrusion 1807 that couples with a clip 1809 (e.g., a snap fit configuration) in the first layer 1806. In some configurations, the second layer 1808 can form an airtight or substantially airtight seal with the first layer 1806. In other configurations, the second layer 1808 does not necessarily create an airtight seal with the first layer 1806. This detachable system can be employed with any of the double mask assemblies described above or elsewhere herein. By being able to detach the second layer it can advantageously be easier to clean the mask and remove water that is trapped between the layers.

Figure 21:
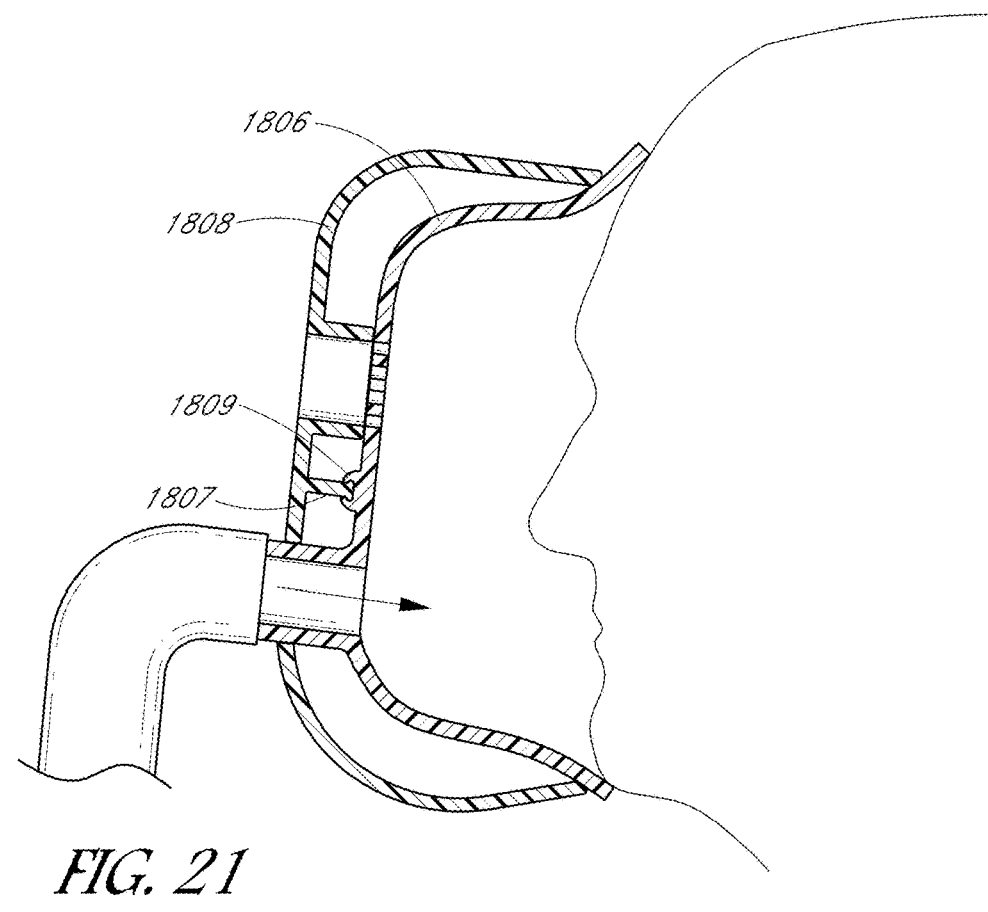
Figure 22:
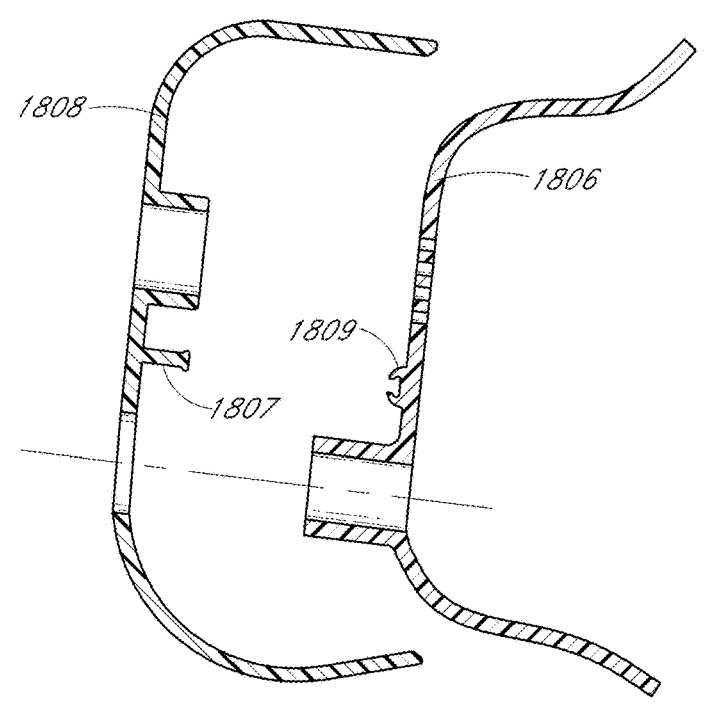
Figures 23, 24:
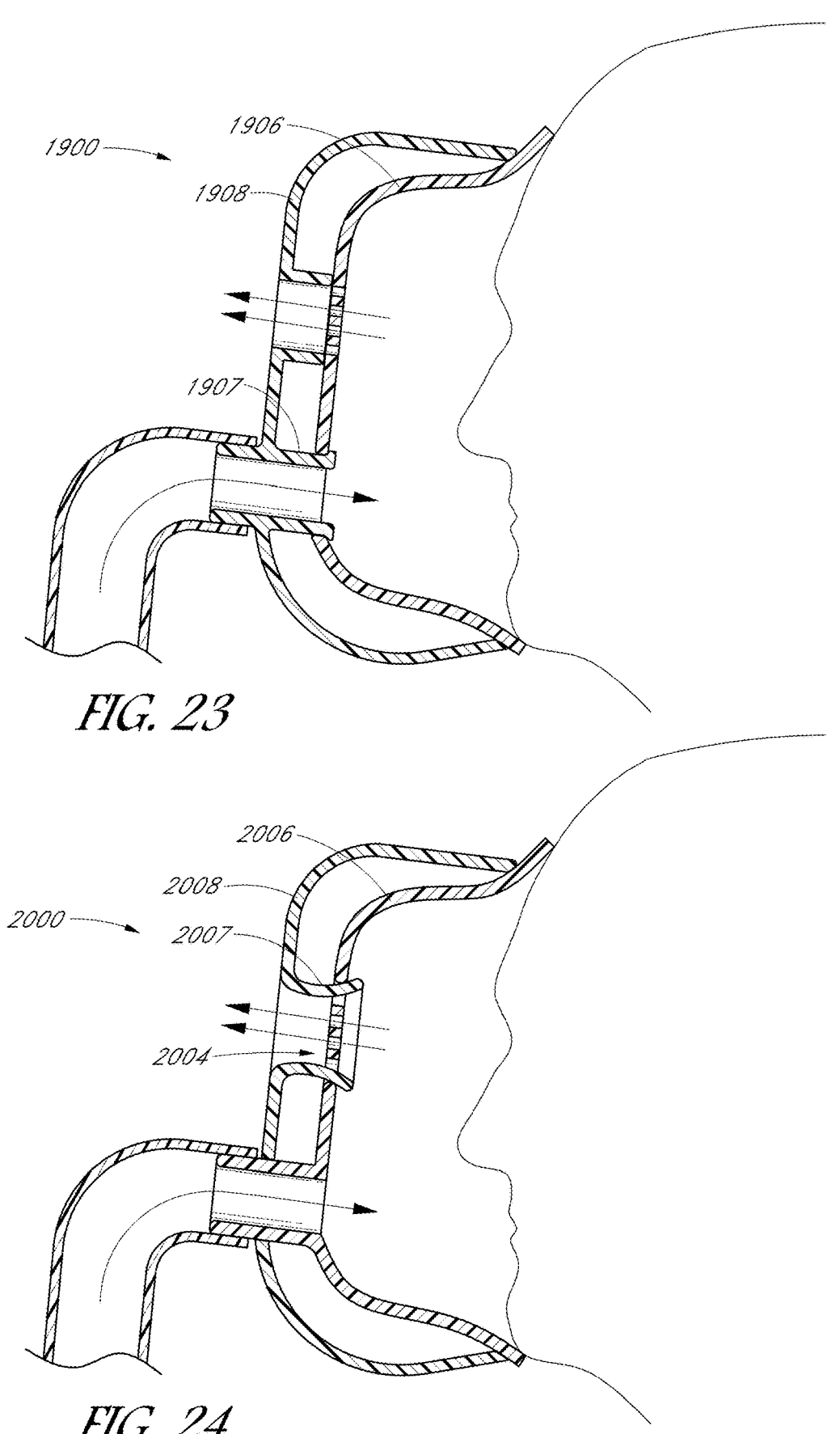

The mask assembly 1900 of FIG. 23 is similar to the mask assembly of FIGS. 21 and 22, but with a different coupling mechanism. The mask assembly 1900 does not have a protrusion and clip to attach the second layer 1908 to the first layer 1906. Instead, the second layer 1908 has a tube connection 1907 that can clip or otherwise couple onto the first layer 1906.

The mask assembly 2000 of FIG. 24 is similar to the mask assembly of FIG. 23 except the coupling mechanism comprises a connection 2007 on the second layer 2008 which clips or otherwise couples into the first layer 2006 of the mask assembly near the vent holes 2004. The connection 2007 can provide a pathway for the fluid exiting the vent holes 2004.

Figures 25, 26:
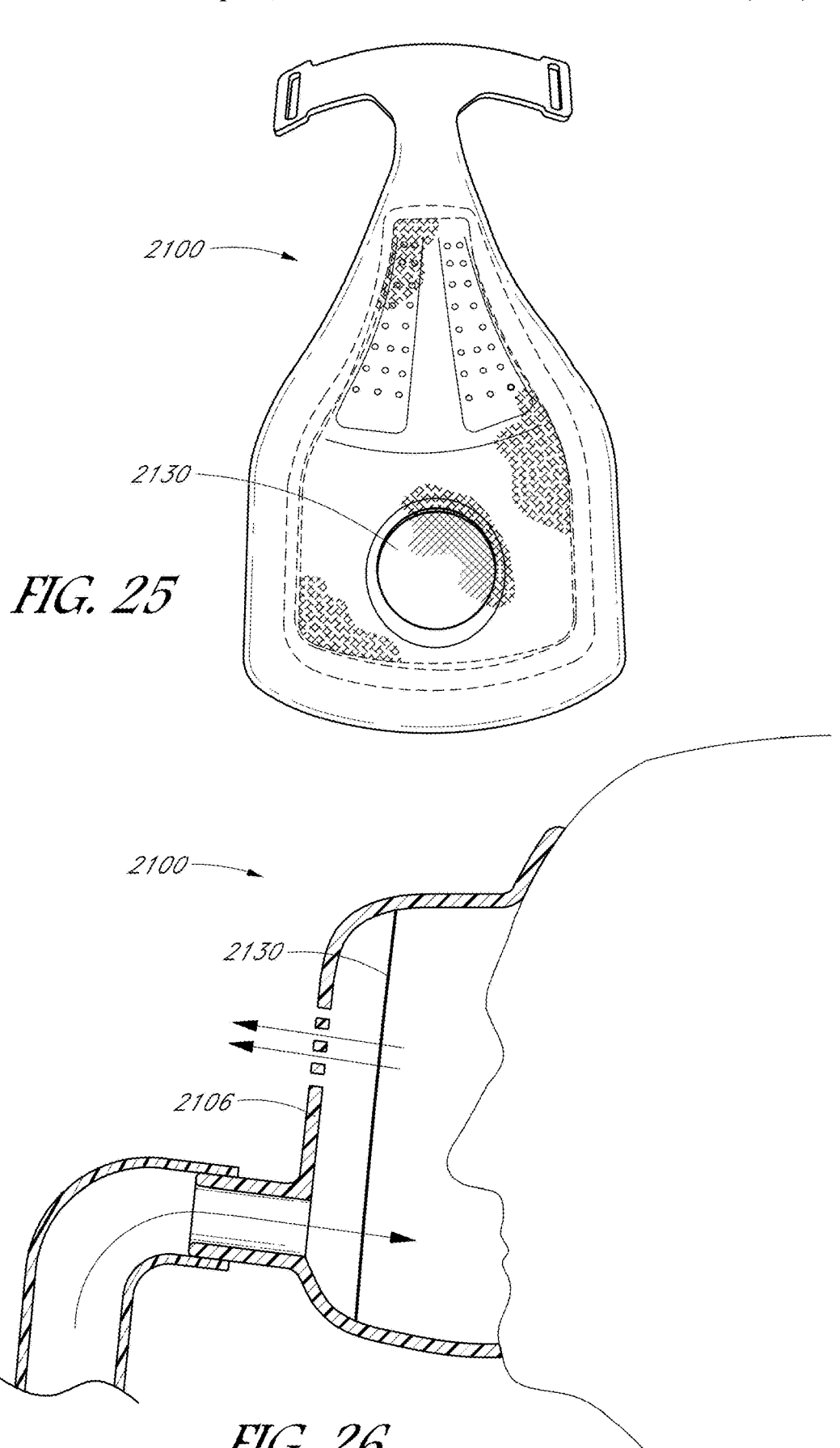
FIG. 25 is a front view of a mask assembly with a breathable membrane layer, according to an embodiment of the present disclosure.
FIGS. 26 and 27 are cross-sectional side views of mask assemblies with breathable membrane layers, according to various embodiments of the present disclosure.

FIGS. 25 and 26 illustrate mask assemblies 2100 incorporating a water vapor breathable membrane layer 2130. Preferably, the membrane layer comprises a water impermeable material which is substantially air permeable. The membrane layer can be a single material or a composite of several layers of material. The material can be non-woven or woven. The membrane layer 2130 can be positioned within the mask assembly 2100 between the mask frame 2106 and the patient's face. Preferably, the membrane layer 2130 does not permit water to pass through the material in liquid form, but permits water vapor to pass through. Thus, the membrane layer 2130 can inhibit or prevent water condensate on the outer side of the membrane layer (i.e., between the mask frame 2106 and membrane layer 2130) from passing through the membrane layer and dripping onto the patient's face.

FIGS. 27-32 and 43 illustrate mask assemblies incorporating a water vapor breathable material layer or membrane, which can be a single layer of material or a composite of multiple layers of material.

Figure 27:
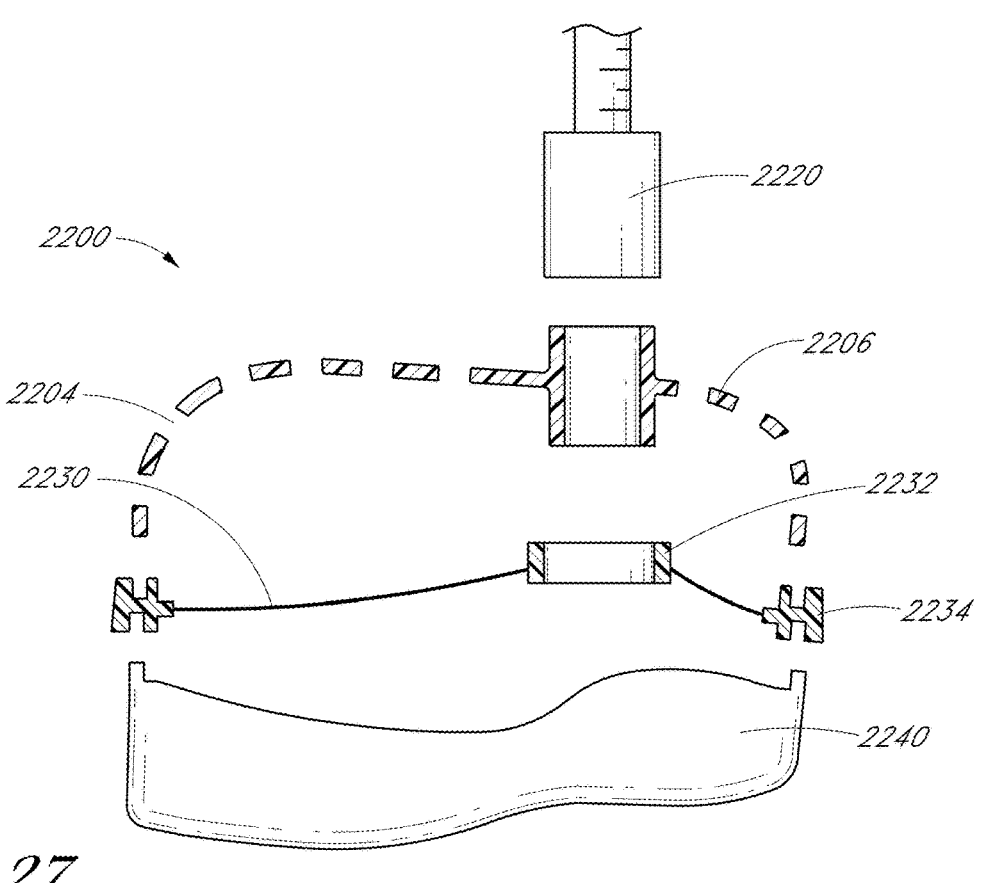
Figure 28:
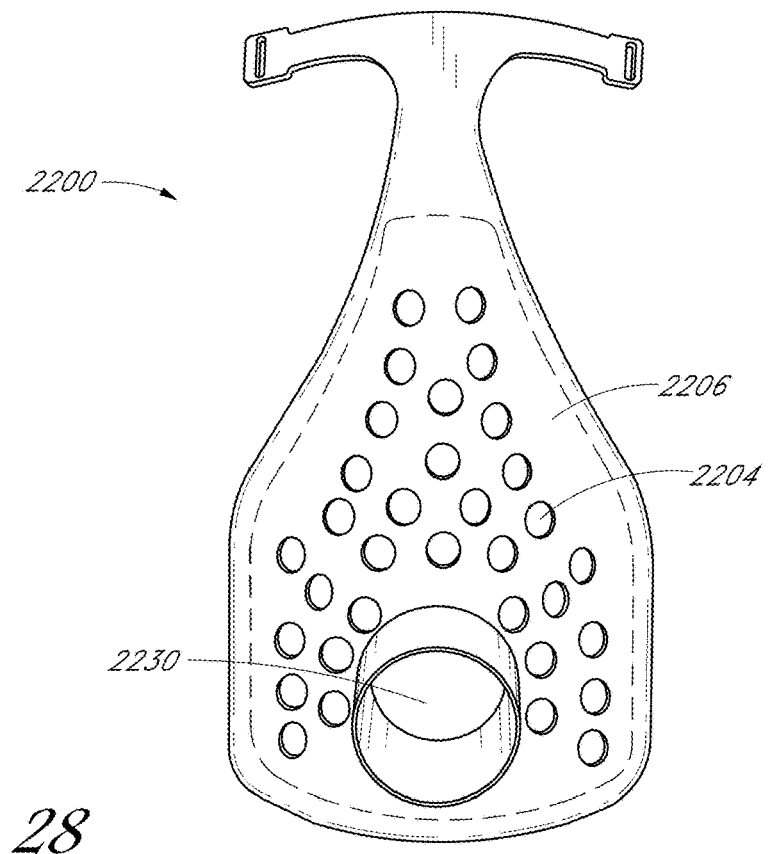
FIG. 28 is a front view of the mask assembly of FIG. 27.

With respect to FIGS. 27 and 28, mask assemblies 2200 incorporating a removable water vapor breathable membrane layer 2230 are illustrated. The breathable membrane layer 2230 can comprise a membrane clamped, clipped-on or otherwise secured onto a small tube 2232 made of plastic or other rigid material. The small tube 2232 can couple to a mask frame 2206 or rigid shell layer, which can then be connected to the breathing tube 2220. The breathable membrane layer 2230 can also have a perimeter structure 2234 that is a rigid or relatively rigid material (e.g., plastic) attached to the exterior perimeter of the membrane material. The perimeter structure 2234 can be configured to couple to a mask seal 2240 (e.g., silicone seal) on one side and a mask frame 2206 (e.g., polycarbonate shell or other suitable rigid material) on the other side. The mask frame 2206 can have vent holes 2204 to allow passive air ventilation while maintaining its rigidity so that the shape and structure of the mask assembly is preserved, giving protection to the breathable membrane layer 2230.

Figures 29, 30:
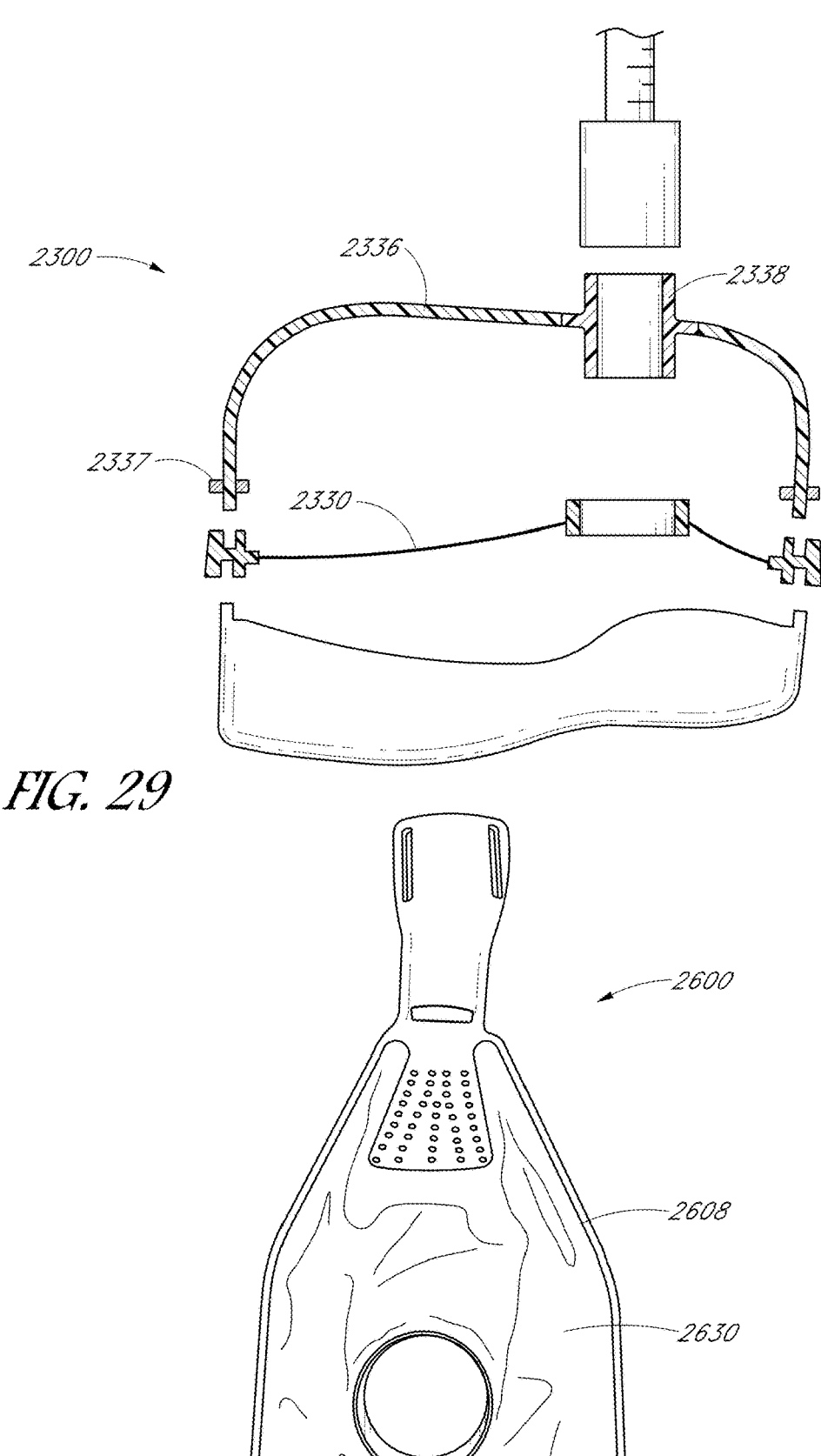
FIG. 29 is a cross-sectional side view of a mask assembly with multiple membrane layers, according to an embodiment of the present disclosure.
FIG. 30 is a front view of a mask assembly with a cut-out portion, according to an embodiment of the present disclosure.
Figures 31, 32:
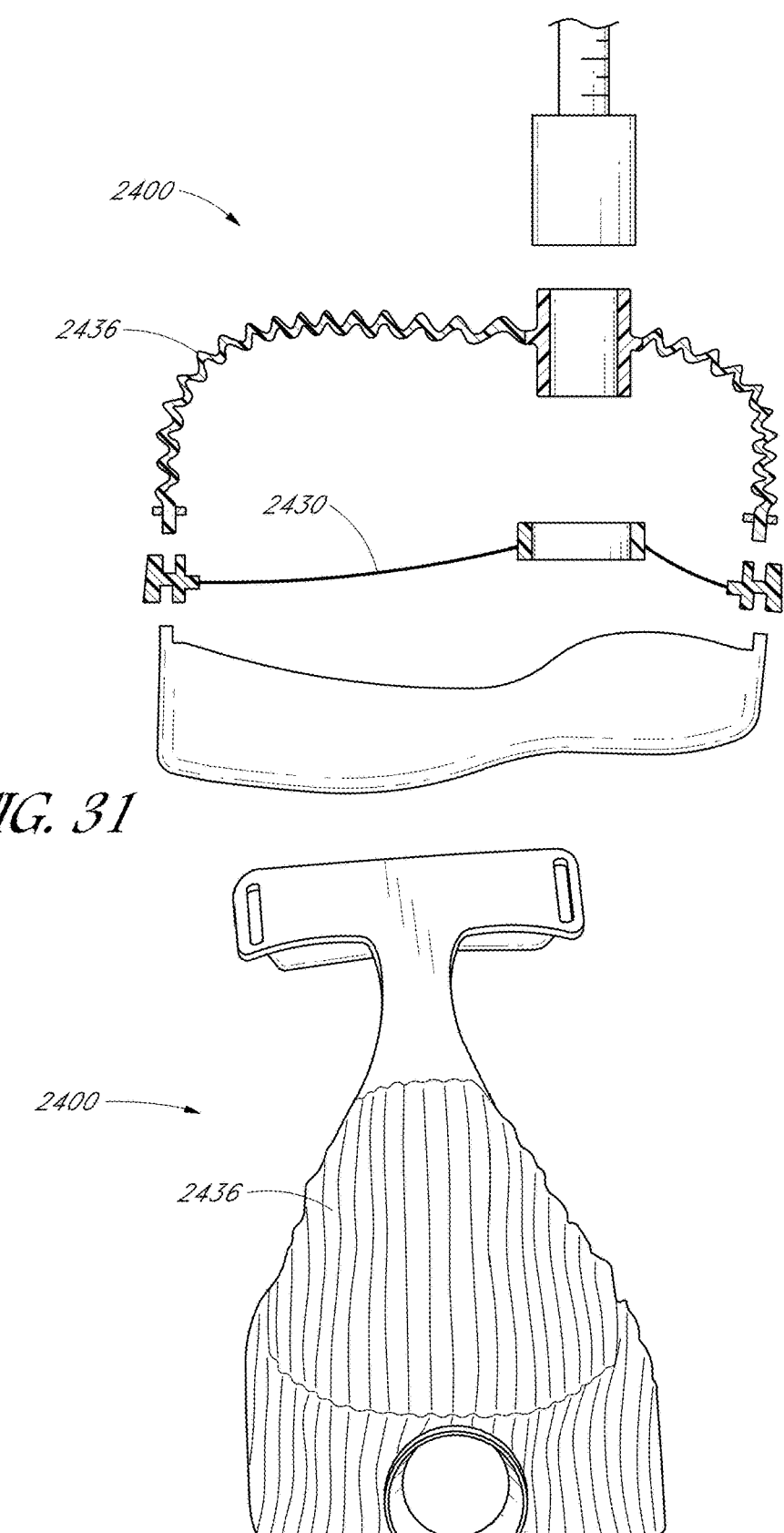
FIG. 31 is a cross-sectional side view of a mask assembly with a ribbed membrane layer, according to an embodiment of the present disclosure.
FIG. 32 is a front view of the mask assembly of FIG. 31.

FIGS. 29, 31, 32 and 43 illustrate mask assemblies 2300 incorporating double layers of water vapor breathable membranes or other water vapor breathable layers. The water vapor breathable membranes can be similar to or the same as in the mask assemblies of FIGS. 27 and 28. However, in place of the mask frame, the illustrated mask assemblies 2300 can have a second membrane layer 2336, which can provide insulation and water vapor breathability to the exterior surface of the mask assembly 2300. In the illustrated configurations, the second membrane layer 2336 is a foamed water vapor breathable membrane layer. By being foamed, the water vapor breathable membrane can be more rigid and can form a robust exterior structure for the mask assembly. Since the foamed water vapor breathable membrane may expand when wet, preferably the second membrane layer 2336 has a perimeter structure 2337 that is a rigid or relatively rigid material (e.g., plastic) attached to the exterior perimeter of the second membrane layer. The second membrane layer 2336 can also have a small tube 2338 made of plastic or other rigid material that can connect to the breathing tube. As illustrated in FIG. 29, the first membrane layer 2330 can connect to the second membrane layer 2336.

The foamed water breathable material 2436 can also be extruded into a ribbed shape (FIGS. 31 and 32) to allow extra surface area for water to evaporate off of and provides additional strength and rigidity.

Figure 43:
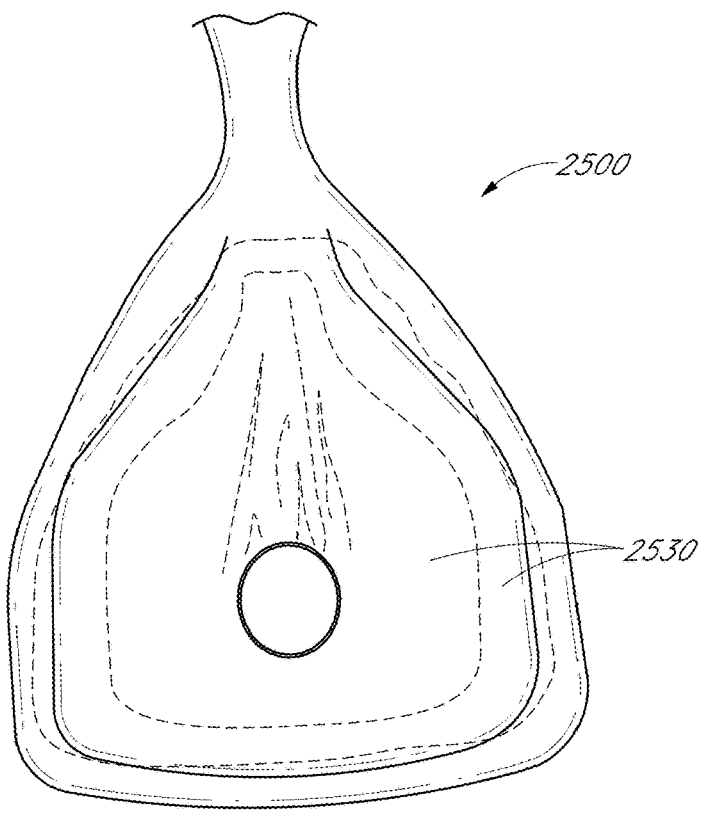
FIG. 43 is a front view of a mask assembly with two membrane layers, according to an embodiment of the present disclosure.
Figure 44:
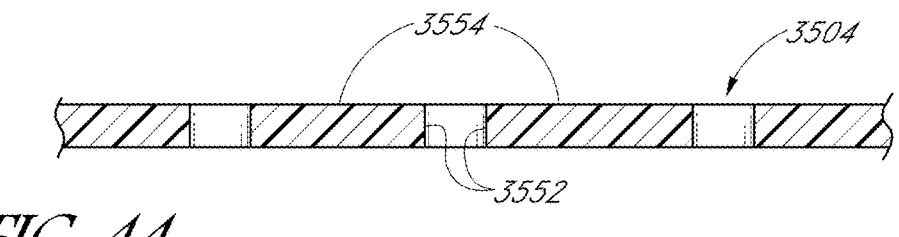
FIG. 44 is a close-up cross-sectional side view of vent holes with hydrophobic and hydrophilic coatings, according to an embodiment of the present disclosure.

Instead of having a foamed water vapor breathable membrane layer, FIG. 43 illustrates a configuration with two membrane layers 2530 that provide insulation to the mask assembly 2500 as well as water vapor breathability.

FIG. 30 illustrates a mask assembly 2600 having a window(s) or a cut-out portion(s) 2608 covered by a breathable material 2630 (e.g., a water vapor breathable membrane). If desired, multiple layers of a breathable material can be employed.

Figures 33, 34:
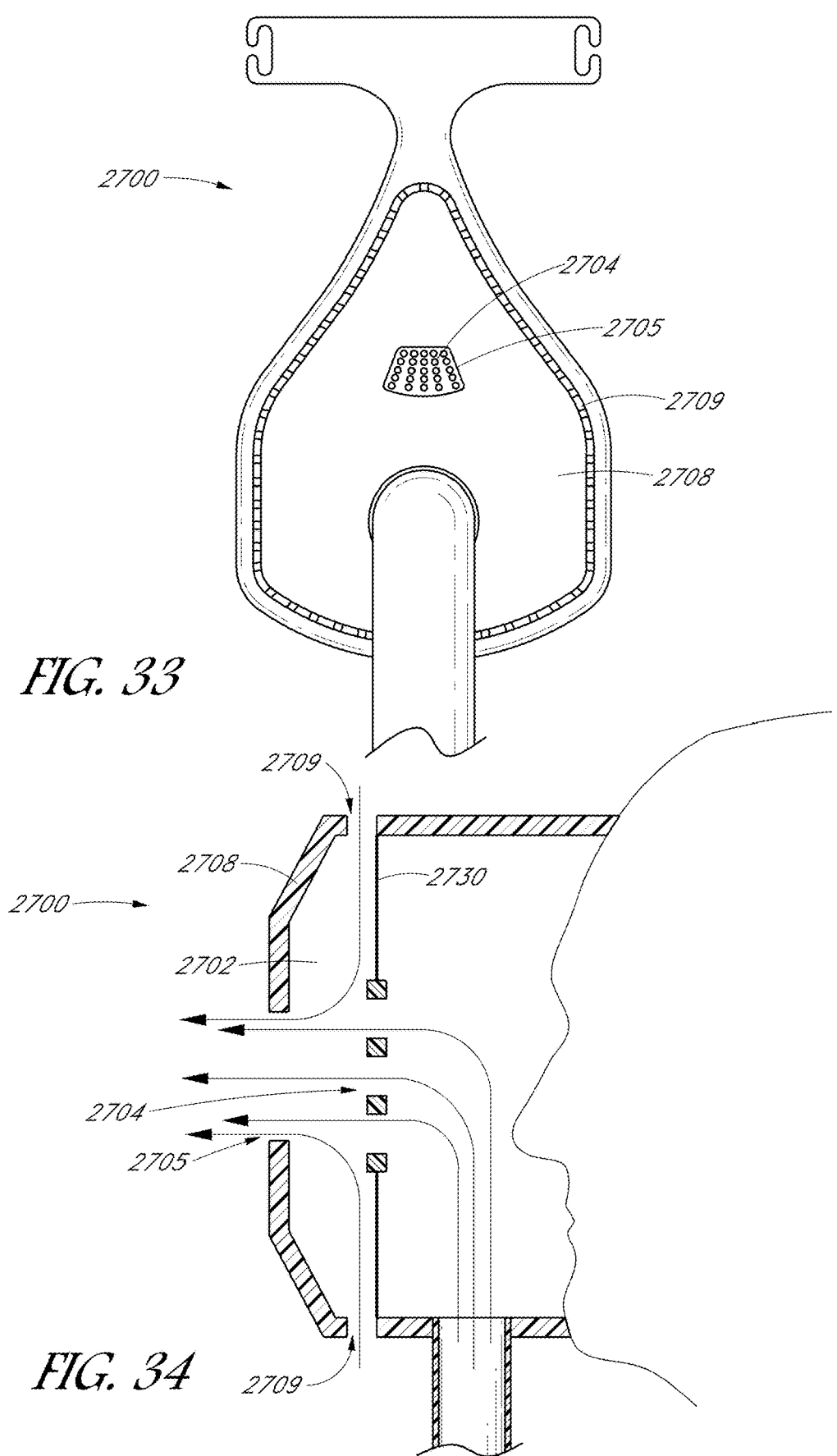
FIG. 33 is a front view of a mask assembly that entrains air, according to an embodiment of the present disclosure.
FIG. 34 is a cross-sectional side view of the mask assembly of FIG. 33.

FIGS. 33-34 illustrate mask assemblies that make use of Bernoulli's principle to actively flow air over the surface of the water vapor breathable material to reduce condensation and FIGS. 35-38 illustrate vents that permit air to be drawn into or otherwise enter the mask assembly to reduce condensation. In some configurations, such as those in FIGS. 33 and 34, the mask assembly 2700 is composed of mostly rigid material (e.g., polycarbonate or other plastics) except for a water vapor breathable membrane layer 2730 which divides the mask assembly into two chambers. Fluids can leave the mask assembly 2700 through recessed vent holes 2704, which can be made of rigid material and clamped, glued, or otherwise attached to the water vapor breathable membrane layer 2730. The fluids can flow out to the environment via a cutout 2705 or other vent holes or exits in the outer shell 2708, which can be made of a rigid plastic. Water vapor can pass through the water vapor breathable membrane layer 2730 and into the intermediary chamber 2702 (space between the water breathable membrane layer 2730 and the outer shell 2708) instead of condensing on the interior surfaces. In the illustrated configurations, entrainment holes 2709 around the perimeter of the outer shell 2708 can suck air in from the environment due to Bernoulli's principle and actively dry the water vapor breathable membrane layer 2730 by moving through the intermediary chamber 2702, and exit through the cutout 2705 near the vent holes 2704.

Figure 35:
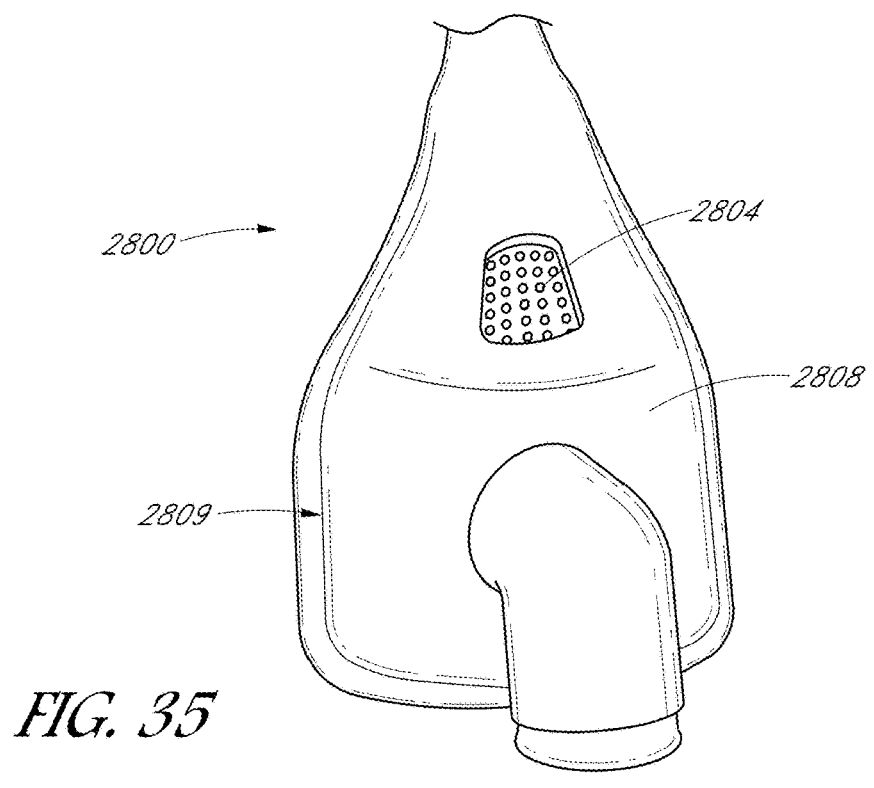
FIG. 35 is a front view of a mask assembly with passive drying, according to an embodiment of the present disclosure.
Figure 36:
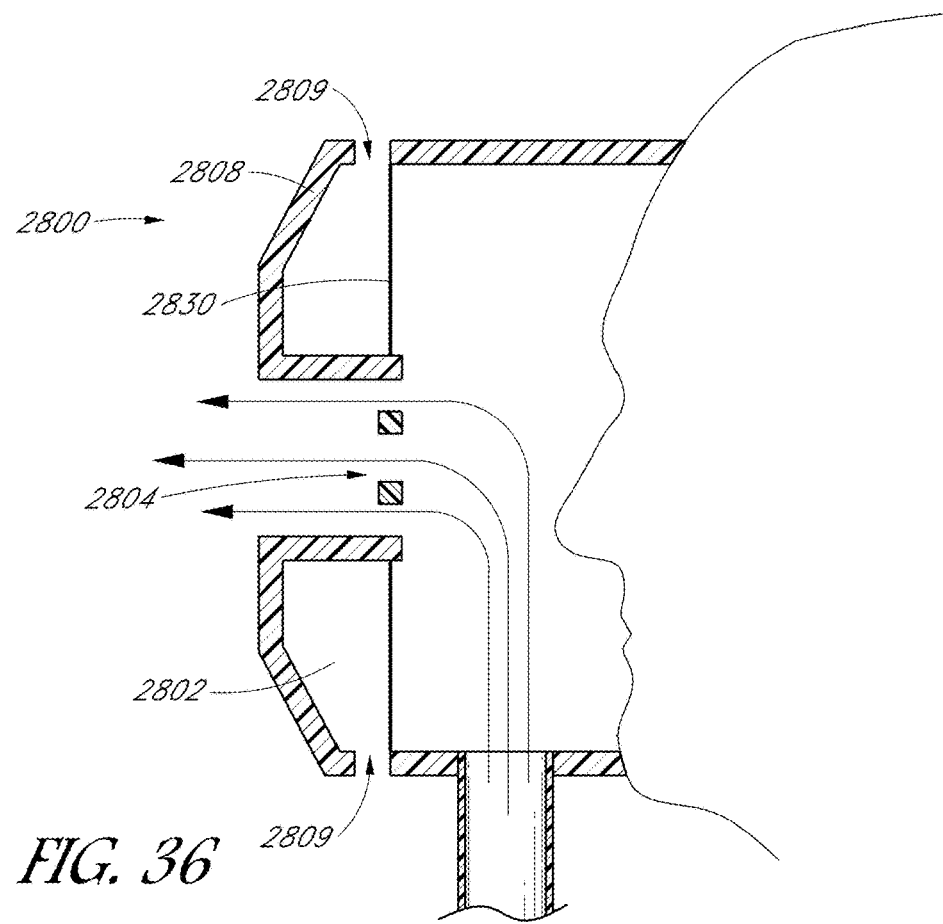
FIG. 36 is a cross-sectional side view of the mask assembly of FIG. 35.

FIGS. 35 and 36 illustrate a mask assembly 2800 with a water vapor breathable membrane layer 2830 and an outer shell 2808. The outer shell 2808 forms a pathway leading from the recessed vent holes 2804 to the environment. The exterior side of the breathable membrane layer 2830 can be dried passively by air entering the intermediary chamber 2802 through drying holes 2809.

Figures 37, 38:
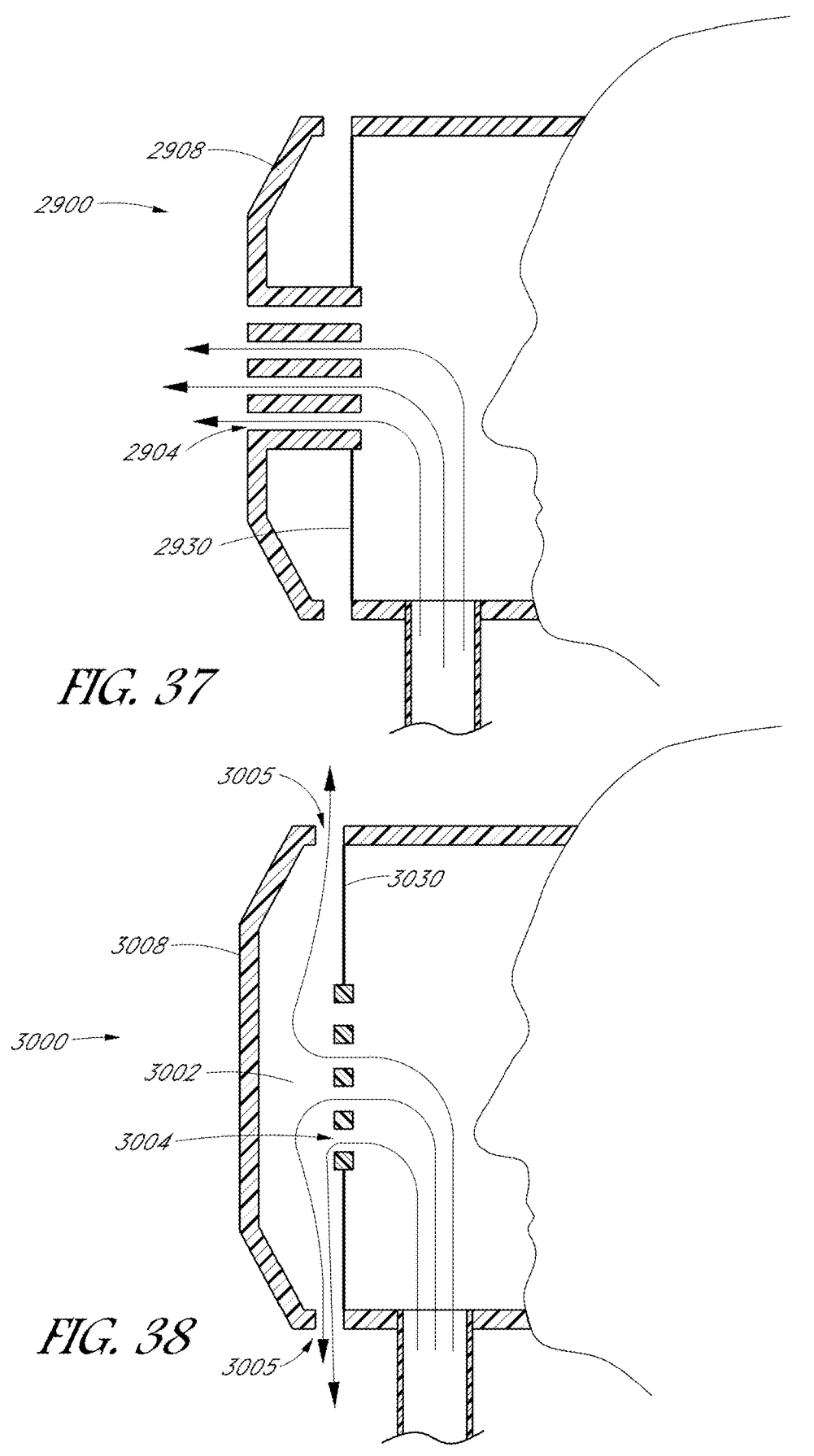
FIGS. 37 and 38 are cross-sectional side views of mask assemblies, according to various embodiments of the present disclosure.

The mask assembly 2900 of FIG. 37 is similar to the mask of FIG. 36 except the vent holes 2904 are not recessed but instead extend from the water vapor breathable membrane layer 2930 to the outer shell 2908.

FIG. 38 illustrates another configuration of a mask assembly 3000 with vent holes 3004 clamped or otherwise coupled to the water vapor breathable membrane layer 3030. Fluids can pass through the vent holes 3004 and into the intermediary chamber 3002. The fluids can then exit the mask assembly 3000 via exhaust holes 3005 around the perimeter of the outer shell 3008.

Figures 39, 40:
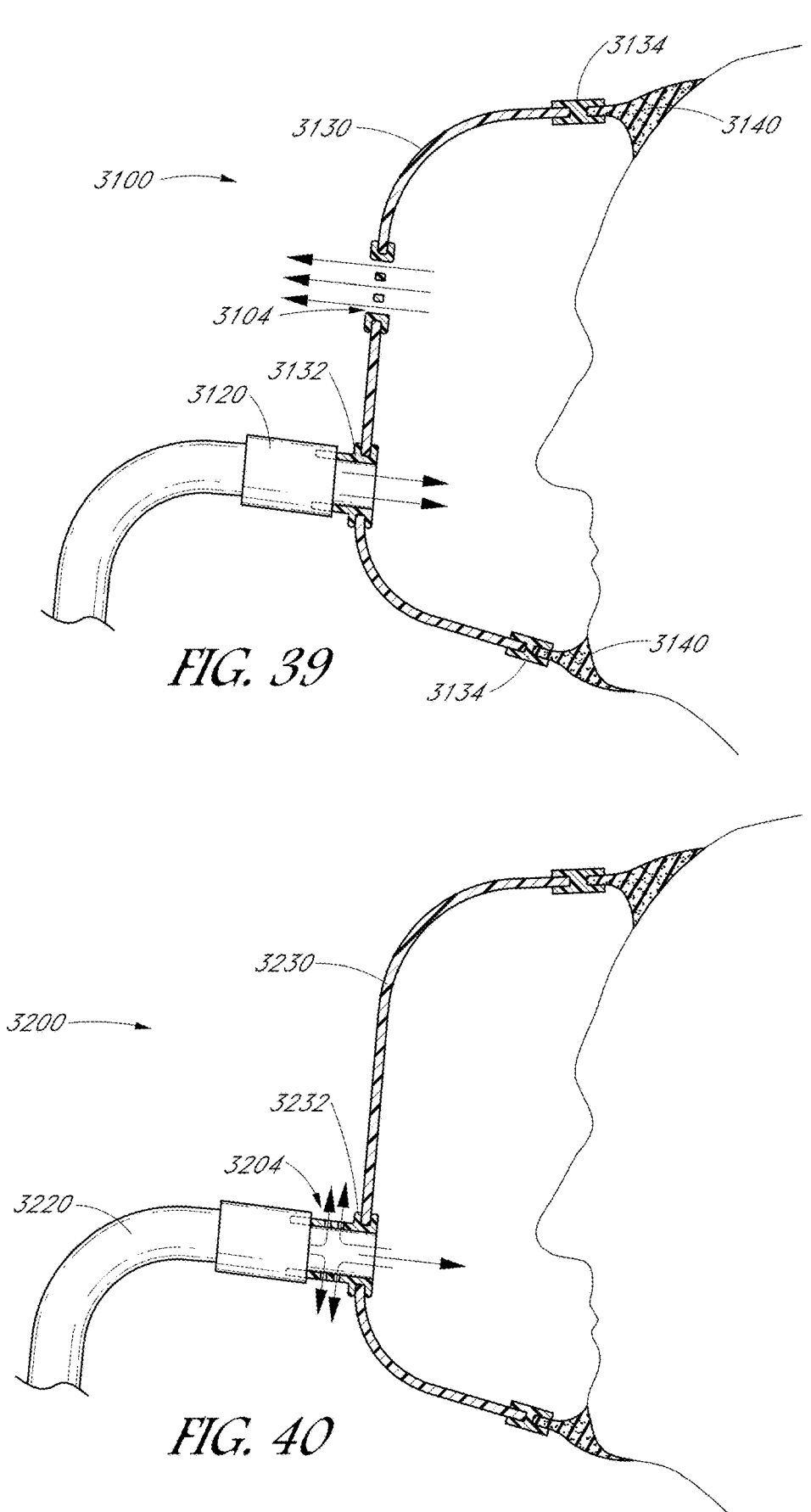
FIGS. 39-42 are cross-sectional side views of mask assemblies with foamed breathable membranes, according to various embodiments of the present disclosure.

FIGS. 39-42 illustrate mask assemblies in which a substantial portion or the majority of the mask assemblies are made out of foamed water vapor breathable membrane material with rigid materials on certain portions of the mask assemblies. FIG. 39 illustrates a configuration of such a mask assembly 3100. A perimeter structure 3134, preferably made of rigid material (e.g., polycarbonate or other plastics), can be clamped or otherwise attached to the breathable membrane 3130 at the perimeter. A seal 3140 (e.g., silicone) can be attached to the perimeter structure 3134 to form an airtight or substantially airtight seal with the patient's face. A connection tube 3132, made of for example rigid plastic, can also be clamped or otherwise attached to the breathable membrane 3130 and configured to couple to the breathing tube 3120. Another rigid piece with vent holes 3104 can also be clamped or otherwise attached to the breathable membrane 3130.

FIG. 40 illustrates another configuration of a mask assembly 3200 with foamed water vapor breathable membrane 3230 that is similar to the mask of FIG. 39. In this configuration, the vent holes 3204 are not in a separate piece of rigid material but instead built into the connection tube 3232 to the breathing tube 3220.

Figures 41, 42:
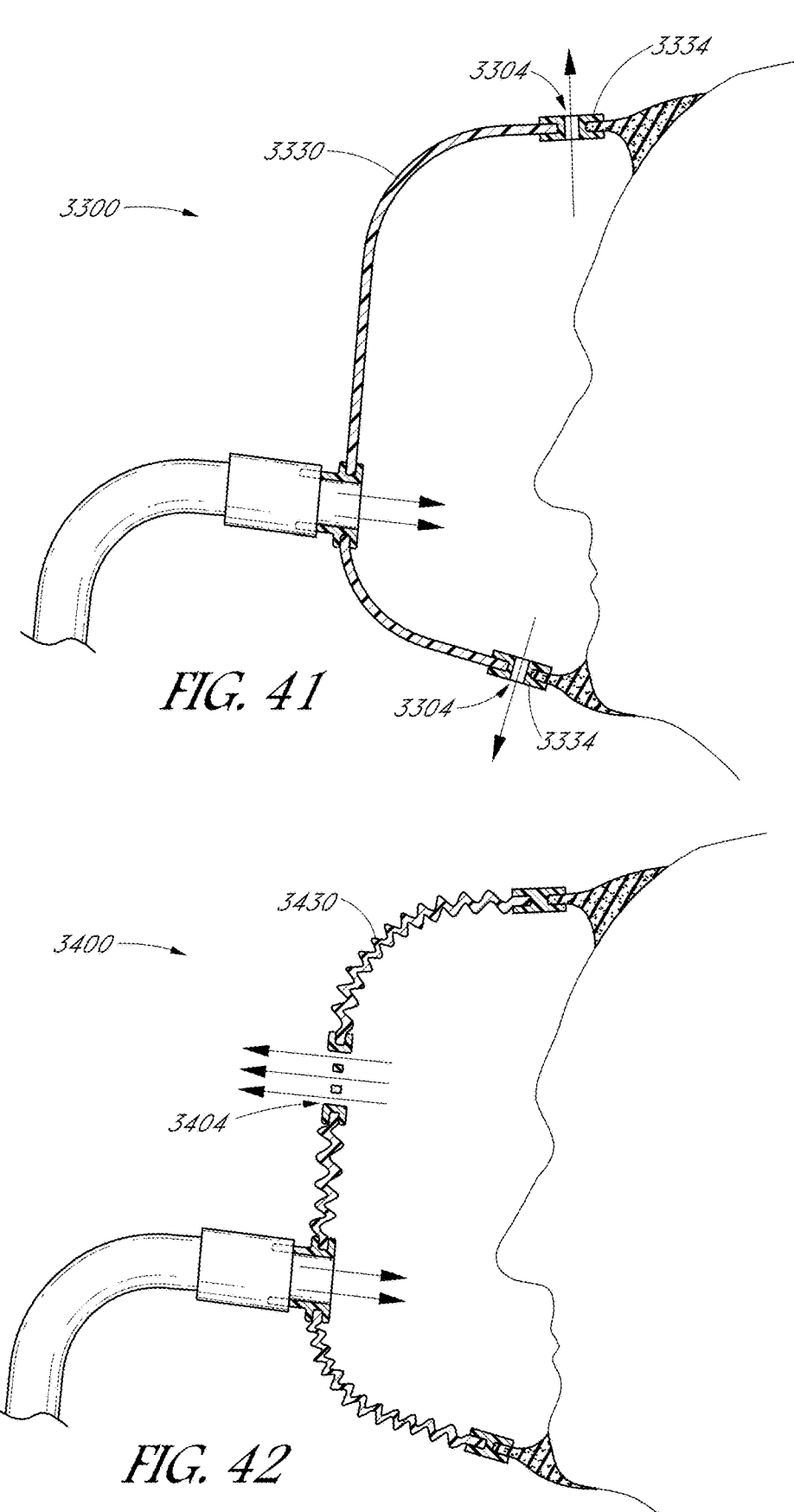

FIG. 41 illustrates a mask assembly 3300 with breathable membrane 3330 that is similar to the mask assemblies of FIGS. 39 and 40, except the vent holes 3304 are located all around the perimeter of the mask assembly in the perimeter structure 3334.

FIG. 42 illustrates a mask assembly 3400 that is similar to the mask assembly of FIG. 39 except the foamed water vapor breathable membrane 3430 is extruded or otherwise formed to be ribbed, thus providing additional surface area for water to evaporate off of. In the illustrated configuration, the vent holes 3404 are disposed on a rigid piece that is attached to the breathable membrane 3430.

FIGS. 44-47 illustrate mask assemblies and portions thereof incorporating hydrophobic and/or hydrophilic materials, coatings or inserts. With respect to FIG. 44, the interior 3552 of the vent holes and, optionally, just at the edge of the vent holes 3504 can be covered in a hydrophobic coating and the surrounding area 3554 of the vent holes can be covered in a hydrophilic coating. This configuration can encourage or facilitate water to move away from the vent holes 3504 and move to the surrounding areas 3554, thereby helping to inhibit or prevent the vent holes 3504 from being clogged up with water. In some configurations, the hydrophobic coating is very hydrophobic whereas the hydrophilic coating can be only slightly hydrophilic so that water is drawn away from the vent holes but does not accumulate too much water.

Figure 45:
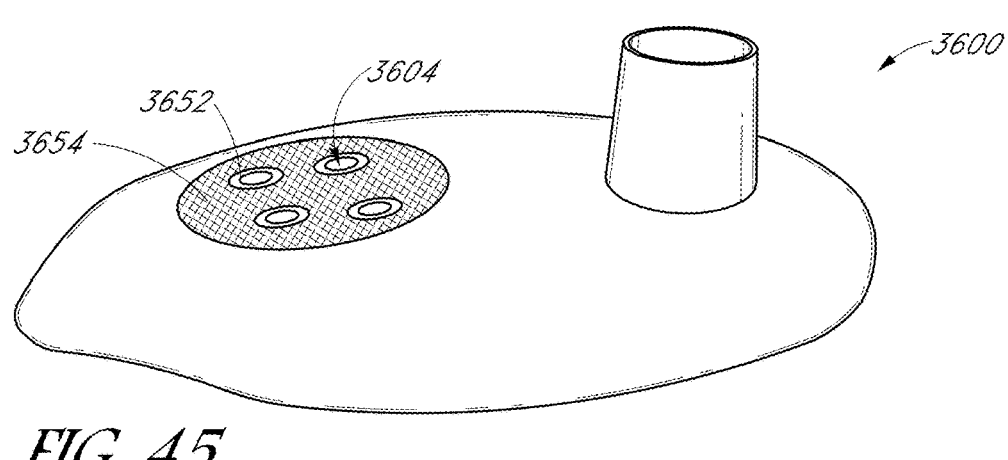
FIG. 45 is a perspective view of a mask assembly with hydrophobic and hydrophilic inserts, according to an embodiment of the present disclosure.

FIGS. 45 and 46 illustrate portions of a mask assembly 3600 with hydrophobic inserts 3652 placed into the vent holes 3604 and hydrophilic inserts 3654 placed around the vent holes 3604. FIG. 46 is a cross-section view of the inserts of FIG. 45.

FIG. 47 illustrates another configuration of a mask assembly 3700 in which the vent holes 3704 are peaks and the surrounding area 3754 are depressions. The vent holes 3704 can be hydrophobic and the surrounding area 3754 can be hydrophilic. The peaks of the vent holes 3704 can allow any accumulated condensation to roll down into the hydrophilic region where the water will be away from the vent holes 3704 and not occlude them. In some configurations, the hydrophilic region can also be designed as channels to carry water further away from the vent holes.

A mask assembly that has extra insulation (e.g., a thicker plastic shell, or a mask covered or coated in an insulating material such as rubber or polar fleece or any other suitable insulation material) can be used to reduce, prevent or compensate for condensation. A mask assembly with extra insulation could also include a mask assembly with a removable soft material cover. Accordingly, the mask assembly can (as an alternative or in addition to other condensation reducing or compensating configurations) incorporate a material (e.g., insulation) layer, which can be permanently or removably secured to the base mask.

Figure 50:
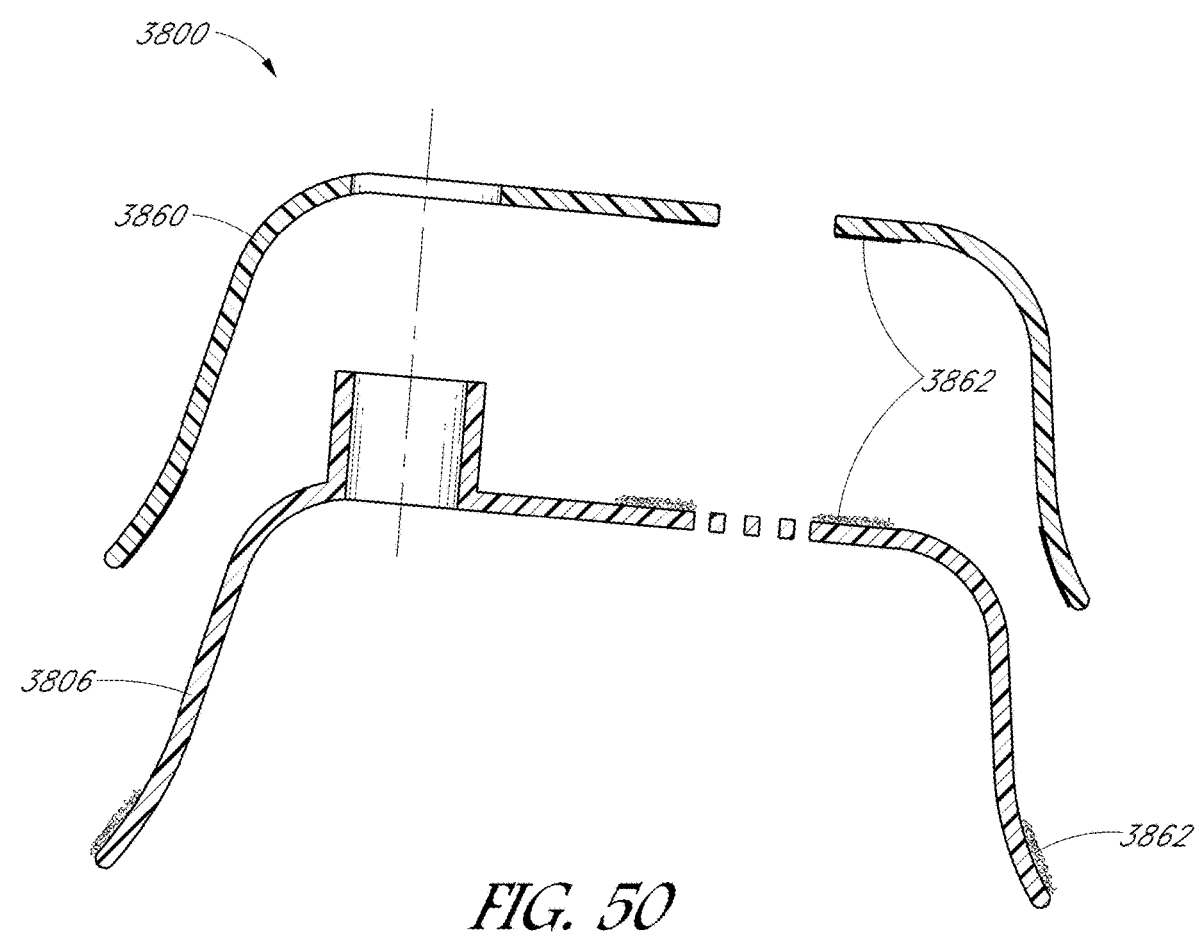
FIG. 50 is an exploded cross-sectional side view of a mask assembly with retaining mechanisms, according to an embodiment of the present disclosure.

FIG. 50 illustrates a mask assembly 3800 with an insulating layer 3860 (e.g., a soft fabric cover) that can attach onto a rigid mask frame 3806. The insulating layer 3860 can be attached using any of a variety of coupling mechanisms 3862, including Velcro® patches, buttons, clasps, zips, string, elastic or other suitable coupling configurations. The insulating layer 3860 can provide any one or combination of additional insulation, a better tactile feel to the mask, as well as the ability to add colours/patterns to the mask assembly.

Figures 51, 52:
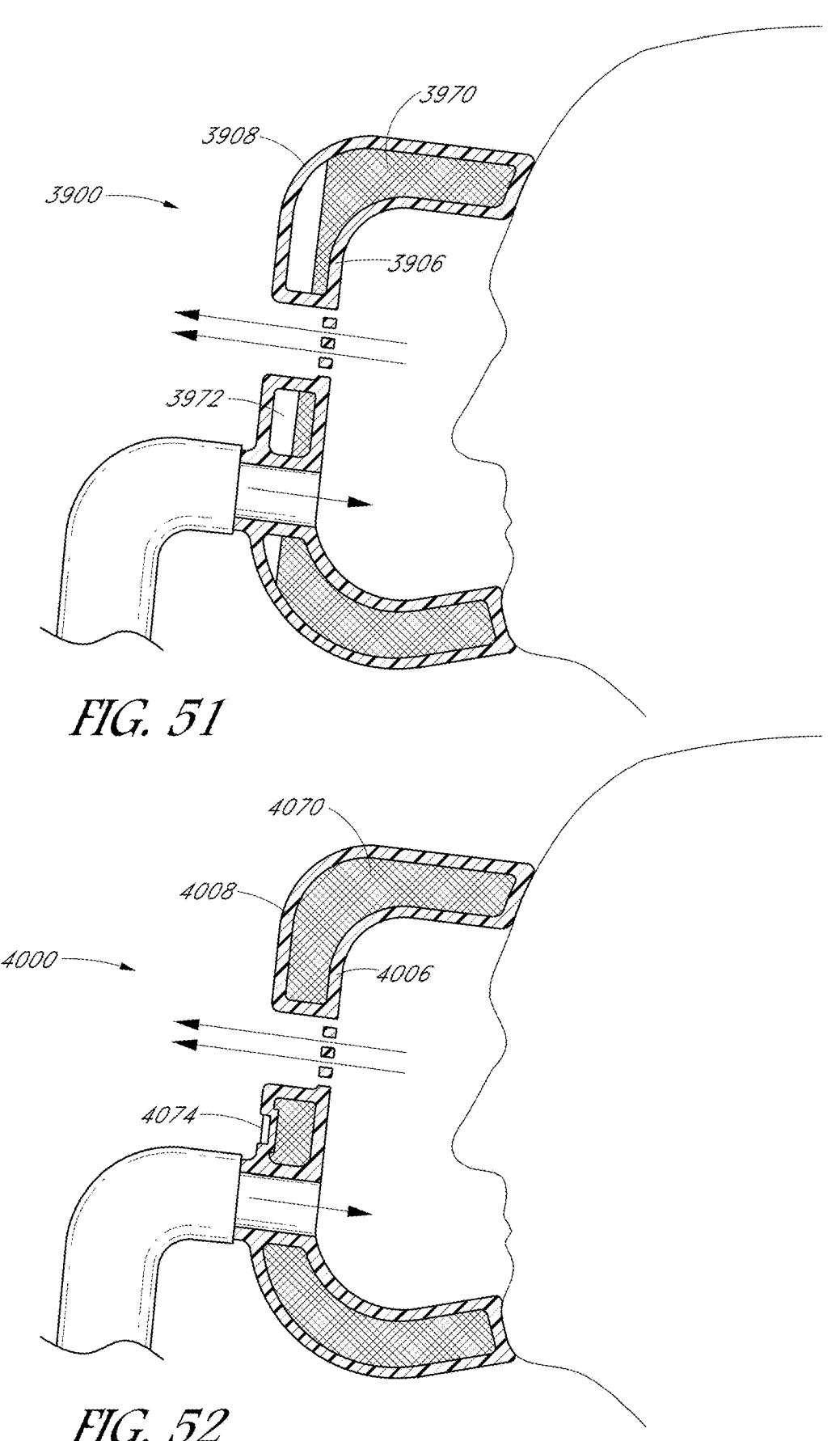
FIGS. 51-53 are cross-sectional side views of mask assemblies with phase change materials, according to various embodiments of the present disclosure.

FIG. 51 illustrates a multi-layer mask assembly 3900 with a phase change material 3970 between the layers 3906, 3908. The phase change material 3970 can be completely sealed off from the rest of the mask to prevent contaminants entering the phase change material or phase change material leaking out. In some configurations, the phase change material 3970 can be a hydrated salt or salt-based solution which has well defined phase change temperatures and good thermal conductivity. However, other appropriate phase change materials can also be used. Some examples of suitable phase change materials include, but are not limited to: PCM-HS34PEES or PCM-HS29P as sold by RGEES LLC, and MPCM32 or MPCM28 as sold by Microtek Laboratories, Inc. In some configurations, the phase change material is able to be heated safely in a microwave. Other heating methods may be employed by the user to heat the phase change material.

The multi-layer mask assembly containing the phase change material can be heated before use so that the phase change material changes phase, such as melting from a solid to a liquid. The phase change material absorbs heat as it changes phase to liquid. The phase change material can subsequently cool until it reaches its phase change temperature and maintain this temperature until all of the material solidifies once again. Only then will the temperature of the phase change material drop below its phase change temperature. For at least the period during which the phase change material is changing phase from liquid back to solid is the period during which the phase change material can be used to maintain the mask assembly at a warm temperature, preventing condensation from forming.

In some configurations, the phase change material can change phase between liquid to solid within the range of 29-35 degrees. This range allows the mask assembly to remain warm enough to at least partially prevent condensation but not so hot as to be uncomfortable to the wearer of the mask assembly. Other temperature ranges are also envisaged. The phase change material can have a high latent heat and, preferably, there is enough of the phase change material provided between the mask layers to allow at least about a 6 hour period (preferably more than 8 hour period) during which the phase change material maintains its temperature before completely solidifying. This allows the phase change material to heat the mask for the majority of a night or typical sleeping period. The time period that temperature is maintained can also be prolonged by adding extra insulation to the exterior of the mask assembly to slow the energy loss to the environment. In some configurations, the mask assembly 3900 can have a small air gap 3972 or other accumulator within the phase change material layer so as to accommodate the increased volume of the phase change material as it changes phase.

FIG. 52 illustrates a multi-layered mask assembly 4000 with supercooled phase change materials 4070 such as sodium acetate enclosed between its layers 4006, 4008. The mask assembly 4000 can be heated to melt the phase change material 4070. As it returns to room temperature the phase change material 4070 naturally supercools without solidification or crystallization occurring.

Then, before the patient uses the mask assembly 4000 to go to sleep, they would, for example, press an activation button 4074 to initialize a seed crystal within the phase change material 4070 to form. This would cause a chain reaction, causing the rest of the phase change material to rapidly solidify and begin to release heat. The heat can reduce or prevent condensation occurring on the mask assembly 4000. The mask can be reused by reheating the mask assembly, such as placing it in boiling water, to melt the phase change material 4070.

Figure 53:
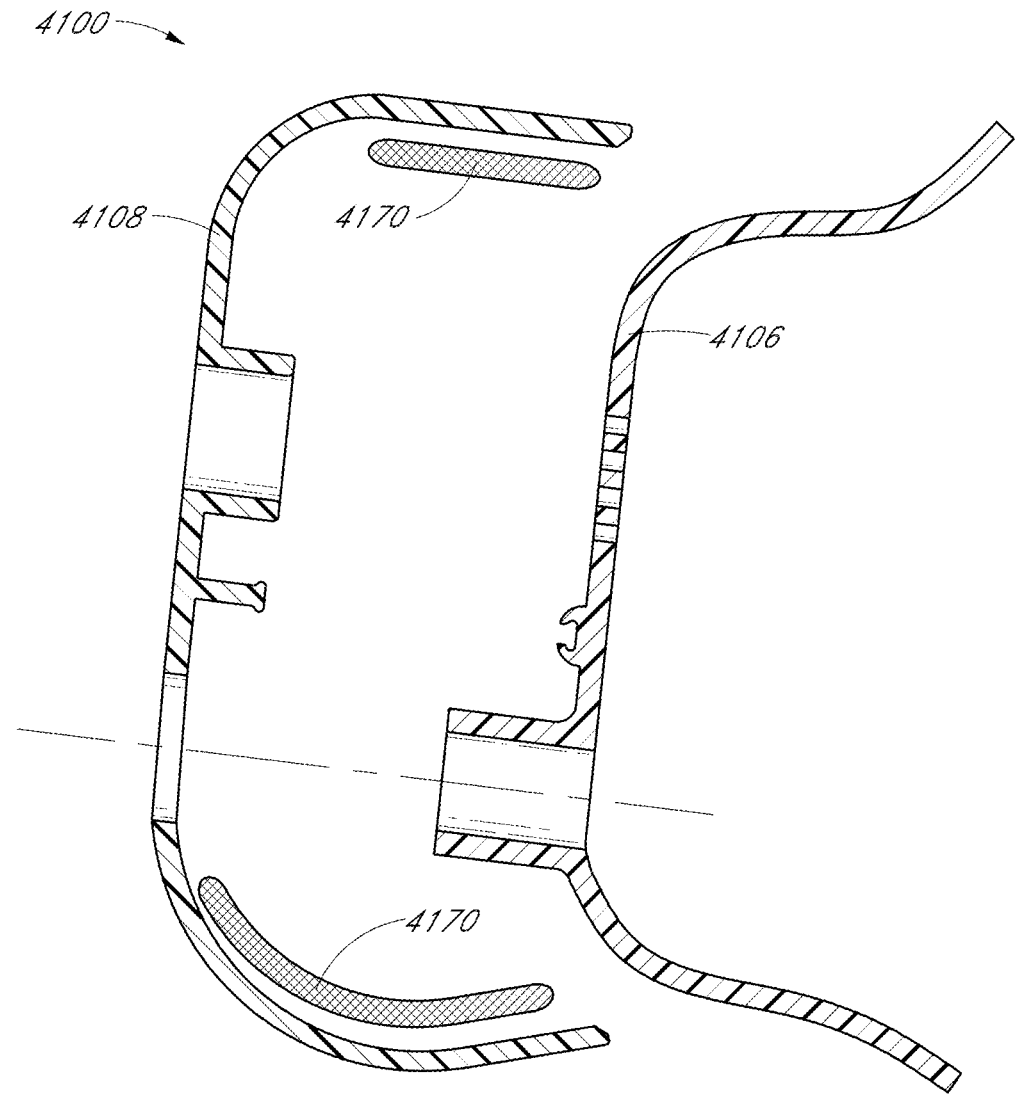

FIG. 53 illustrates a multi-layered mask assembly 4100 where the second layer 4108 can be detached from the first layer 4106 (i.e., main part) of the mask and a heat pad 4170 can be disposed between the layers. The heat pad 4170 can consist of a phase change material as described above, encapsulated in an appropriate material or bag, or it could be a reversible or irreversible chemical based heat pad, or other suitable heat-producing configuration. In some configurations, the heat pad 4170 can be removable and/or replaceable.

Chemical based heat pads are commonly used to treat sports injuries (such as those sold by http://www.beyondbodiheat.com/Products.aspx). Some heat pads contain iron powder, which when exposed to air cause oxidization to occur and generate heat. These heat pads can produce heat for a long period of time, such as BodiHeat® which generates heat for approximately 12 hours. These heat pads can provide sufficient heat for the duration of a night, but are single use products and need to be replaced every use.

FIGS. 54-58 illustrate mask assemblies comprising of thermally conductive materials. With respect to FIG. 54, a mask assembly 4200 comprises two layers, which can be made of materials such as plastic. The outer layer 4208 can be a conventional insulating layer made of for example plastic, such as polycarbonate. The inner layer 4206 can be a thermally conductive polymer such as those sold by Cool Polymers, Inc. (www.coolpolymers.com). The thermally conductive inner layer 4206 can be warmed by contact with the patient's skin, or by the hot gases emitted by the CPAP device or the patient's lungs. This allows the thermally conductive inner layer 4206 to evenly spread heat to cooler regions of the mask assembly 4200, such as around the ventilation holes 4204, reducing the occurrence of condensation forming. The insulating outer layer 4208 can help slow heat loss to the outside ambient air. Therefore the mask's interior can remain warm with less condensation forming. Some configurations of this mask assembly can comprise a heating element 4210, such as a coiled conductive (e.g., copper) wire in-moulded into one or both of the inner layer 4206 and the outer layer 4208 and extend out of the mask assembly. The heating element 4210 can be electrically charged to produce heat and further warm the mask interior preventing condensation from forming.

Figures 54, 55:
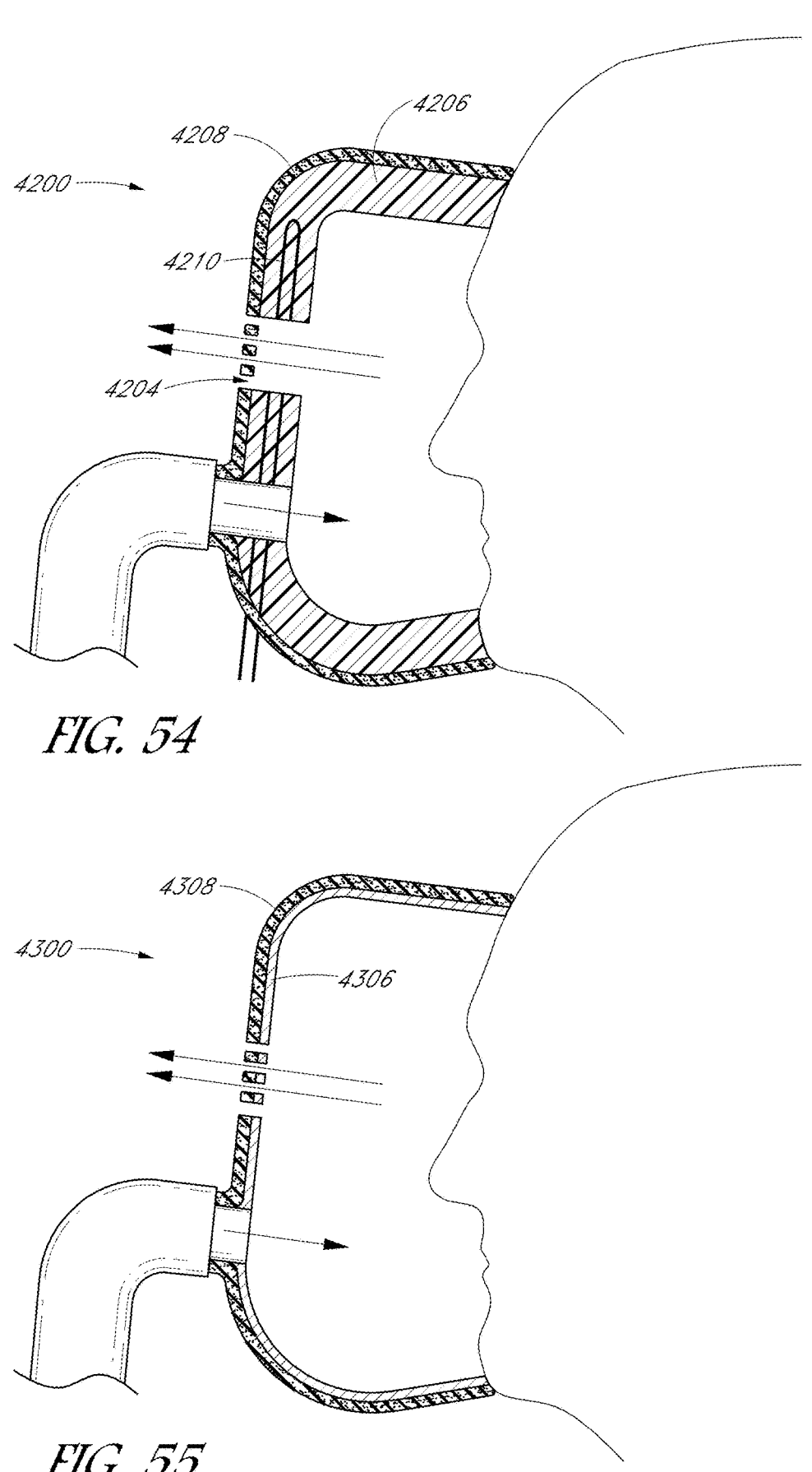
FIGS. 54-55 are cross-sectional side views of mask assemblies with thermally conductive materials, according to various embodiments of the present disclosure.

With respect to FIG. 55 the thermally conductive inner layer 4306 is a thin layer of conductive metal, such as aluminum or other suitable material. The properties of this mask assembly 4300 can be similar to the design illustrated in FIG. 54 but may require less material and be thinner as conductive metals are often more thermally conductive than thermally conductive plastics. However, this mask assembly 4300 configuration may be more difficult and/or expensive to manufacture, and to ensure that the metal layer is held firmly in place by the insulating outer layer 4308.

Figure 56:
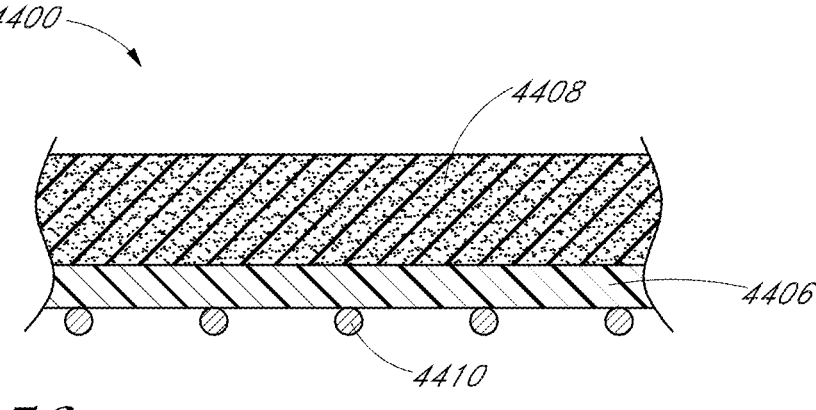
FIG. 56 is a close-up cross-sectional side view of a mask assembly with a heating element and layers, according to an embodiment of the present disclosure.

FIG. 56 illustrates a heating element 4410, such as a coiled and electrically insulated wire, that is attached to the inner layer 4406 (e.g., conductive metal material) of the mask assembly 4400. An insulating outer layer 4408 can be coupled to the inner layer 4406. The heating element 4410 can be electrically charged to produce heat. The conductive inner layer 4406 allows the heat to spread through the mask's surface, reducing or preventing any cold patches or areas of the mask assembly 4400 that the heat from the heating elements cannot reach. With the interior of the mask heated in this manner, less condensation may form.

Figure 57:
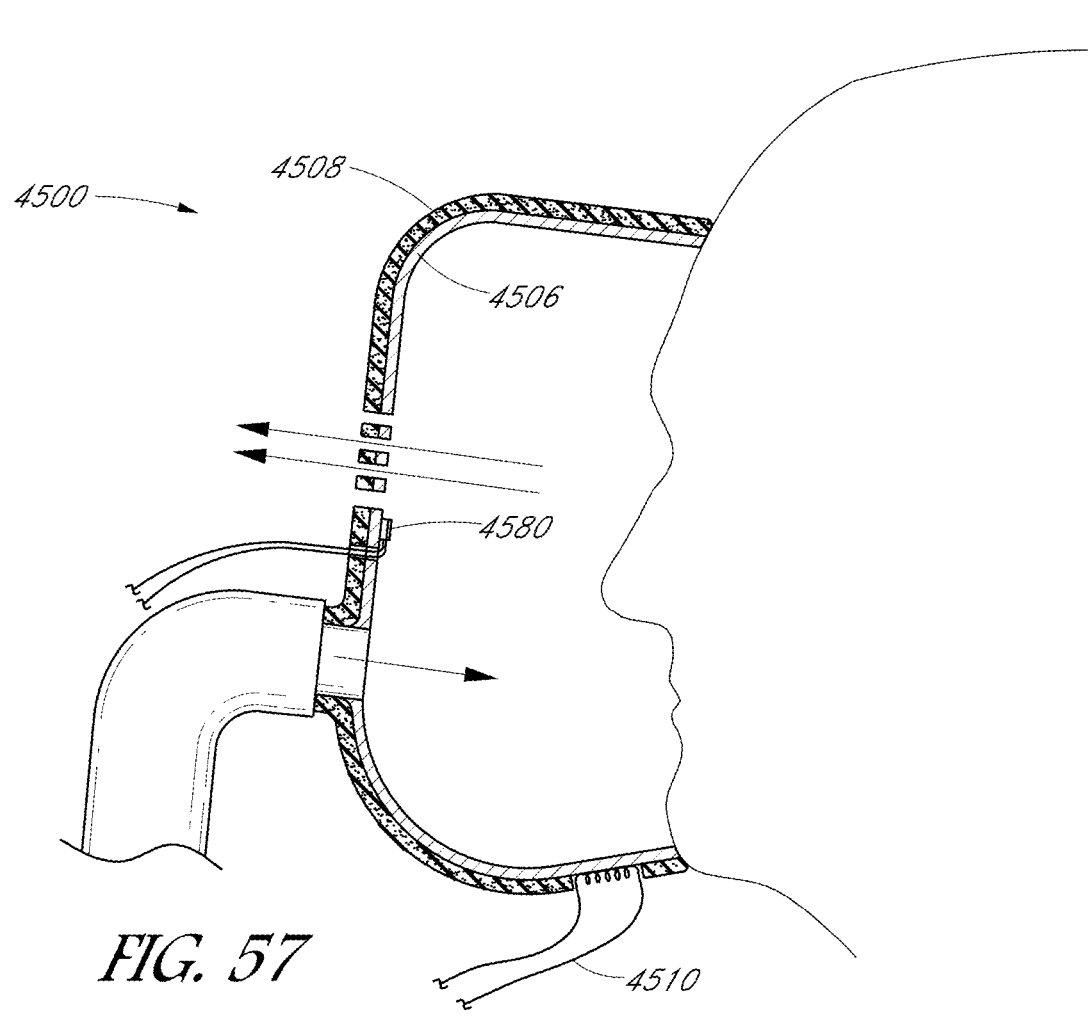
FIGS. 57-58 are cross-sectional side views of mask assemblies with heating elements and sensors, according to various embodiments of the present disclosure.

With respect to FIG. 57, a mask assembly 4500 is illustrated with a patch of the inner layer 4506 exposed through the outer layer 4508. A heating element 4510, such as an insulated copper wire can be coiled and densely packed onto the surface of the exposed inner layer 4506. When an electrical charge heats the heating element 4510, the heat can spread through the conductive inner layer 4506 to a substantial portion of or, preferably, the entirety of the inner layer 4506. A sensor 4580, such as an electrical thermometer, can be placed inside the mask and its measurements can be used in a feedback loop to intelligently control the electrical current sent to the heating element 4510 in order to maintain the inner mask temperature to be above dew point but not so hot as to become uncomfortable to the wearer of the mask assembly.

Figures 58, 59:
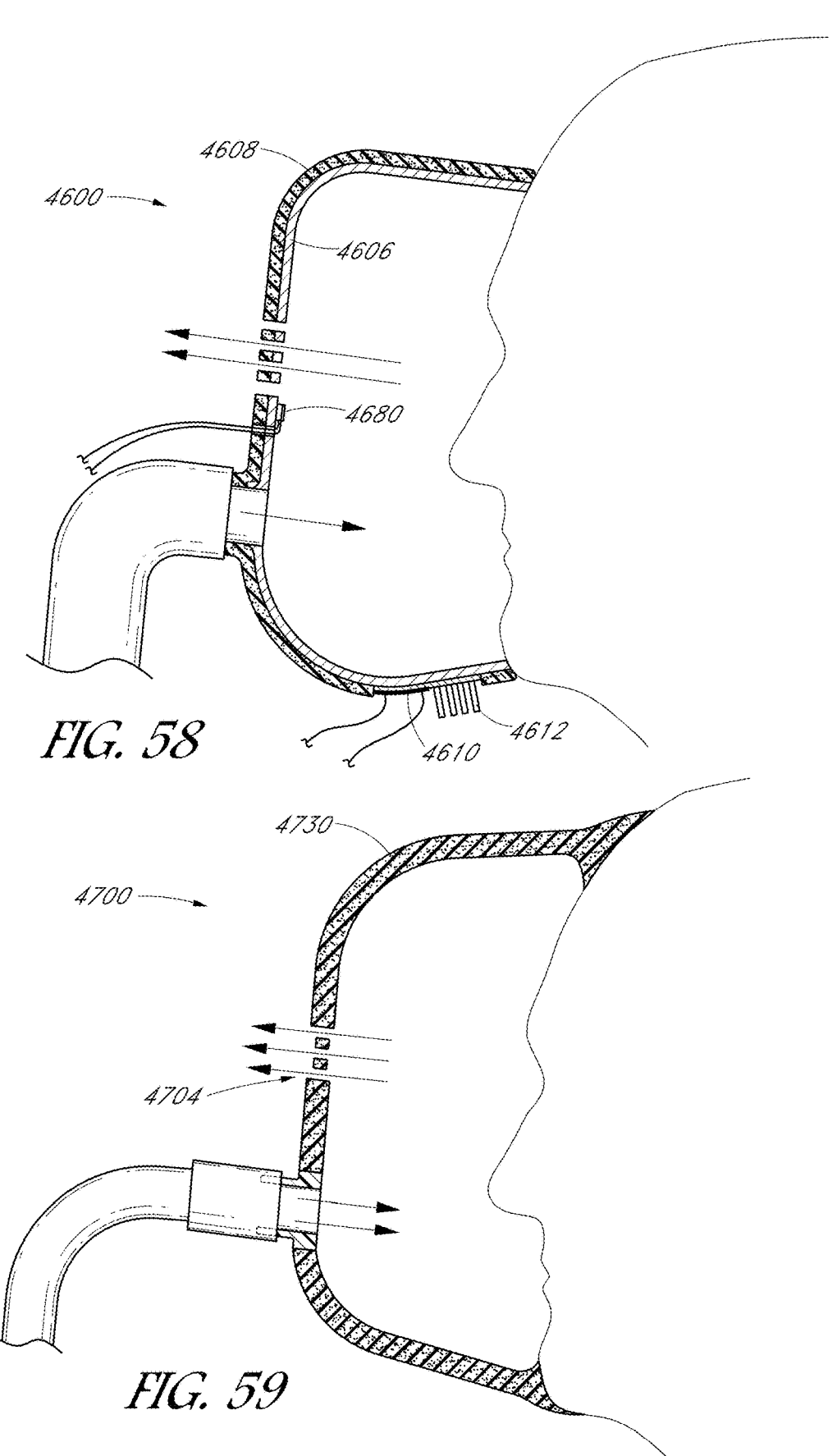
FIG. 59 is a cross-sectional side view of a mask assembly with an insulation layer, according to an embodiment of the present disclosure.

With respect to FIG. 58, a mask assembly 4600 is shown with an outer layer 4608 and an inner layer 4606 with conductive material that can be heated through the use of a thermoelectric cooling device 4610, such as a Peltier cooler. The thermoelectric cooling device 4610 can be placed on the conductive inner layer 4606 so that its hot side is against the conductive material and the cold side is against the air. In some configurations, the cold side can be attached to a heat sink 4612. This can encourage the cold side to return to room temperature faster, thus increasing the efficiency of the thermoelectric cooling device 4610. A sensor 4680, such as an electrical thermometer, can be on the interior surface of the inner layer 4606 of the mask and its readings can be used to control the power sent to the thermoelectric cooling device 4610. This creates a feedback loop that can allow varying currents or no current at all to be sent to the thermoelectric cooling device to ensure the mask interior remains above the dew point but does not become so hot as to become uncomfortable for the wearer of the mask.

In some configurations, the mask assembly can comprise an insulation layer. With reference to FIG. 59, the mask assembly 4700 can have an insulation layer 4730 made of for example foamed plastic. The foamed plastic can be formed using a direct injection expanded foam molding process, which is a foam manufacturing process that can create closed-cell foam products direct from compound to final insulation layer. In some configurations, vent holes 4704 can be integrally formed during the direct injection expanded foam molding process, or formed separately from the process. In some configurations, the insulation layer can be made of other suitable insulated materials, such as rubber or textiles.

Figures 60, 61:
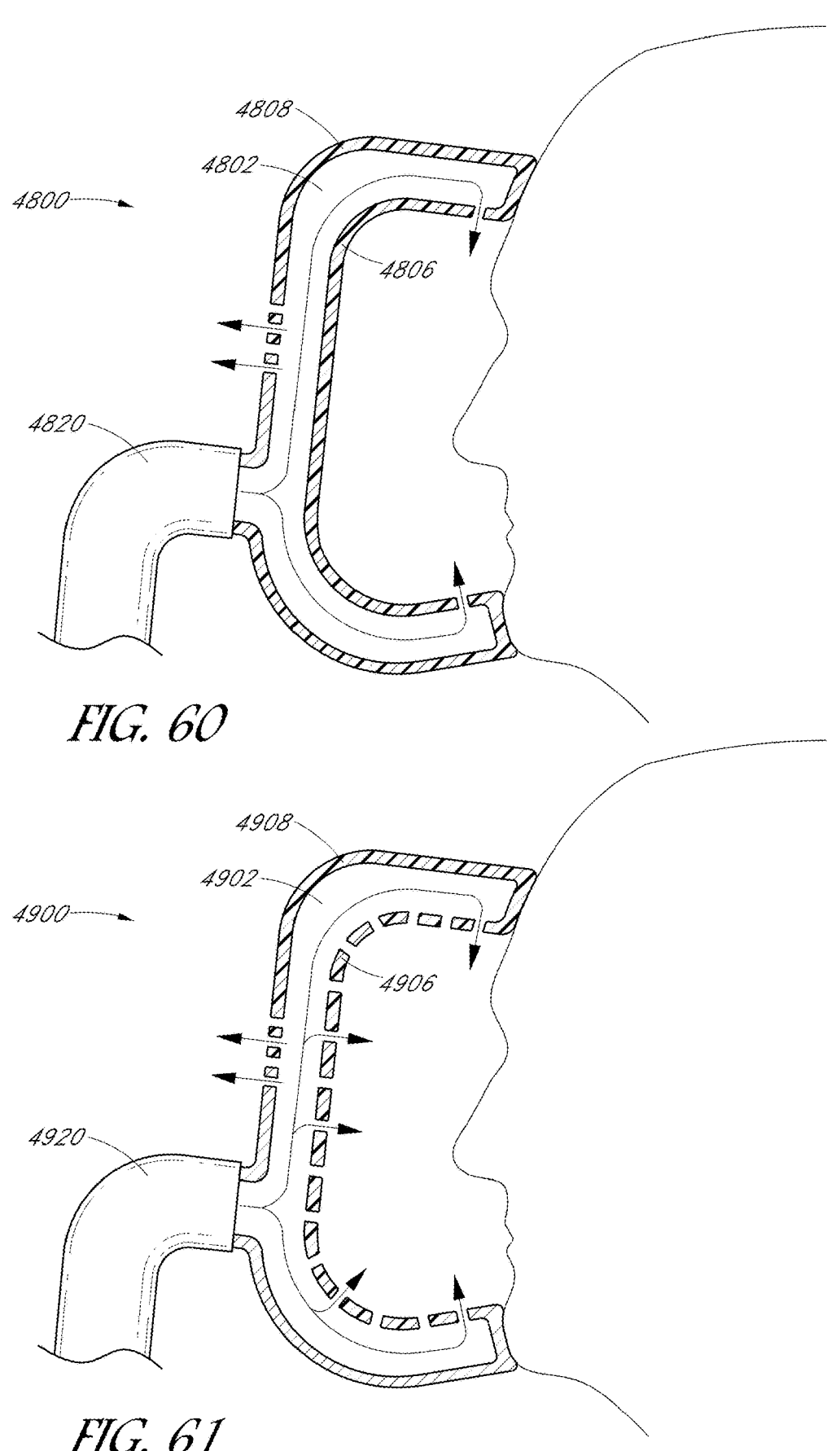
FIGS. 60-61 are cross-sectional side views of mask assemblies with diffusers, according to various embodiments of the present disclosure.

As illustrated in FIGS. 60 and 61, the mask assembly can have an inner layer that diffuses the fluids entering the mask assembly from the gas delivery system. In the configuration illustrated in FIG. 60, the fluids entering the mask assembly 4800 through the breathing tube 4820 travel into the intermediary chamber 4802, which is the space between the inner layer 4806 and the outer layer 4808. The inner layer 4806 obstructs direct flow to the patient so the fluids can flow around the inner layer 4806. The inner layer 4806 can be heated by the fluids from the gas delivery system, which are usually at a higher temperature than ambient air. The heated inner layer 4806 can help reduce the formation of condensation in the mask assembly.

The mask assembly 4900 illustrated in FIG. 61 is similar to the mask assembly of FIG. 60, except the inner layer 4906 comprises one or more holes. Similar to as described above, the fluids entering the mask assembly 4900 through the breathing tube 4920 travel into the intermediary chamber 4902 between the inner layer 4906 and the outer layer 4908. The inner layer 4906 obstructs direct flow to the patient so the fluids can flow around the inner layer 4906 and through the holes in the inner layer 4906. The inner layer 4906 can be heated by the fluids flowing around and through the inner layer 4906. The heated inner layer 4806 can help reduce the formation of condensation in the mask assembly.

In any of the above-described mask assemblies, the vent holes can be replaced or supplemented with elongated holes or slits to inhibit or prevent the holes from clogging with water from condensation.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

Although certain embodiments, features, and examples have been described herein, it will be understood by those skilled in the art that many aspects of the methods and devices illustrated and described in the present disclosure may be differently combined and/or modified to form still further embodiments. For example, any one component of the interfaces or circuits illustrated and described above can be used alone or with other components without departing from the spirit of the present disclosure. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present invention. Thus, it is intended that the scope of the present invention should not be limited by the particular embodiments described above, but should be determined only by a fair reading of the claims that follow.

What is claimed is:

1. A patient interface comprising:
a body adapted to form a seal with a user's face, the body comprising:
an inner layer;
an outer layer;
an insulation space defined by a space between the inner layer and the outer layer; and
a coupling for fluid connection to a gas delivery system;
wherein the insulation space is completely sealed from an interior and an exterior of the patient interface and wherein the insulation space is filled with a fixed mass of a medium at a pressure lower than atmospheric pressure.

2. The patient interface of claim 1, wherein the medium provides an insulating function.

3. The patient interface of claim 2, wherein the medium is a low conductivity fluid.

4. The patient interface of claim 1, further comprising a vent that allows a flow of gases from an interior of the body to an exterior of the body.

5. The patient interface of claim 4, wherein the vent is recessed and disposed adjacent the inner layer.

6. The patient interface of claim 4, wherein the vent comprises a plurality of holes extending from the inner layer to the outer layer.

7. The patient interface of claim 4, configured such that, in use, air in the insulation space is warmer than ambient air and reduces water condensation in the vent.

8. The patient interface of claim 1, further comprising a heating element disposed in the insulation space.

9. The patient interface of claim 8, wherein the heating element comprises a heated wire.

10. The patient interface of claim 1, wherein the inner layer and the outer layer are formed of a plastic material.

11. The patient interface of claim 1, wherein the body comprises a silicone seal member.

12. The patient interface of claim 1, wherein the gas delivery system is configured to deliver heated and humidified air.

* * * * *